(12) United States Patent
Heldman et al.

(10) Patent No.: US 12,228,552 B2
(45) Date of Patent: Feb. 18, 2025

(54) TESTING SYSTEMS, FIXTURES AND METHODS FOR MECHANICALLY TESTING IMPLANTS INCLUDING BREAST TISSUE EXPANDERS

(71) Applicant: Mentor Worldwide LLC, Irvine, CA (US)

(72) Inventors: Lucas Heldman, Wayne, NJ (US); Michael Hoffman, Hillsborough, NJ (US); Hector Javier Toro Estrella, Lake Forest, CA (US)

(73) Assignee: Mentor Worldwide LLC

( * ) Notice: Subject to any disclaimer, the term of this patent is extended or adjusted under 35 U.S.C. 154(b) by 620 days.

(21) Appl. No.: 17/550,639

(22) Filed: Dec. 14, 2021

(65) Prior Publication Data

US 2023/0184650 A1    Jun. 15, 2023

(51) Int. Cl.
*G01N 3/32* (2006.01)
*A61B 90/00* (2016.01)
*A61F 2/12* (2006.01)

(52) U.S. Cl.
CPC .............. *G01N 3/32* (2013.01); *A61F 2/12* (2013.01); *A61B 90/02* (2016.02);
(Continued)

(58) Field of Classification Search
CPC ............. G01N 3/32; G01N 2203/0005; G01N 2203/0019; G01N 2203/003; G01N 2203/0202; G01N 2203/0256; G01N 3/303; G01N 19/00; G01N 19/02; G01N 33/20; A61F 2/12; A61F 2240/008; A61F 2/468; A61F 2/30; A61F 2/4425; A61F 2/30942; A61F 2/34; A61F 2/36; A61B 90/02; A61B 5/0053; A61B 5/4851; A61B 17/1739

See application file for complete search history.

(56) References Cited

U.S. PATENT DOCUMENTS 6,557,426 B2   5/2003   Reinemann, Jr. et al.
10,119,893 B2  11/2018  Feng
(Continued)

FOREIGN PATENT DOCUMENTS

BR   102013027531 A2   9/2016
BR   102013027530 A2   11/2017
WO   2019095409 A1    5/2019

*Primary Examiner* — Brandi N Hopkins
(74) *Attorney, Agent, or Firm* — Troutman Pepper Locke LLP

(57) ABSTRACT

A test fixture for mechanically testing breast implants includes a frame, a base plate coupled with the frame, and a first actuator coupled with the base plate for providing reciprocating motion to the base plate along a first axis. The test fixture includes a compression plate coupled with the frame that opposes the base plate, a second actuator coupled with the compression plate for providing reciprocating motion to the compression plate along a second axis that intersects the first axis, and a third actuator coupled with the compression plate for providing reciprocating motion to the compression plate along a third axis that intersects both the first axis and the second axis. The test fixture includes a control system in communication with the first, second, and third actuators for controlling the movement of the base plate along the first axis and the movement of the compression plate along the second and third axes.

19 Claims, 30 Drawing Sheets

(52) U.S. Cl.
CPC .................. *A61F 2240/008* (2013.01); *G01N 2203/0005* (2013.01); *G01N 2203/0019* (2013.01); *G01N 2203/003* (2013.01); *G01N 2203/0202* (2013.01); *G01N 2203/0256* (2013.01)

(56) References Cited

U.S. PATENT DOCUMENTS

2014/0276230 A1\* 9/2014 Pattison ............... A61B 5/0051
                                                                        600/587
2020/0345477 A1 11/2020 Brandon et al.

\* cited by examiner

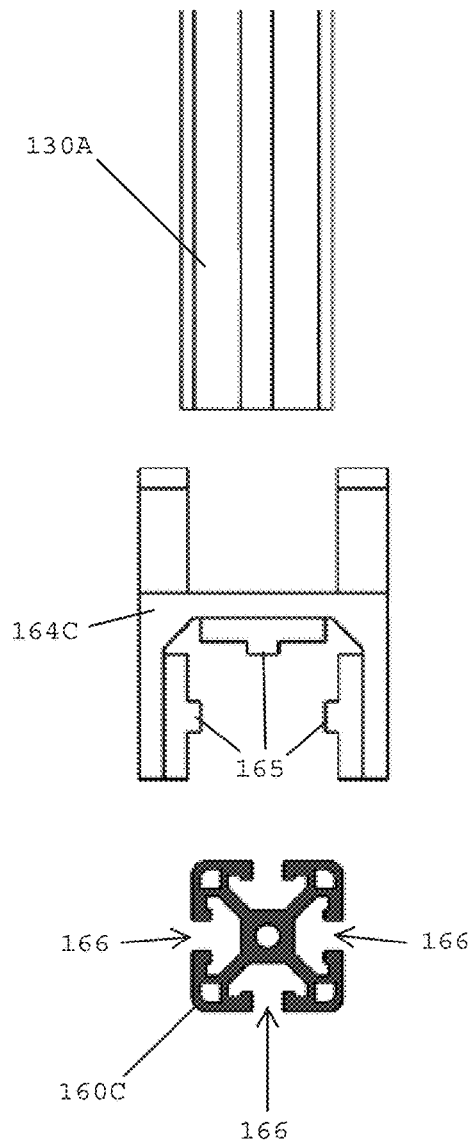
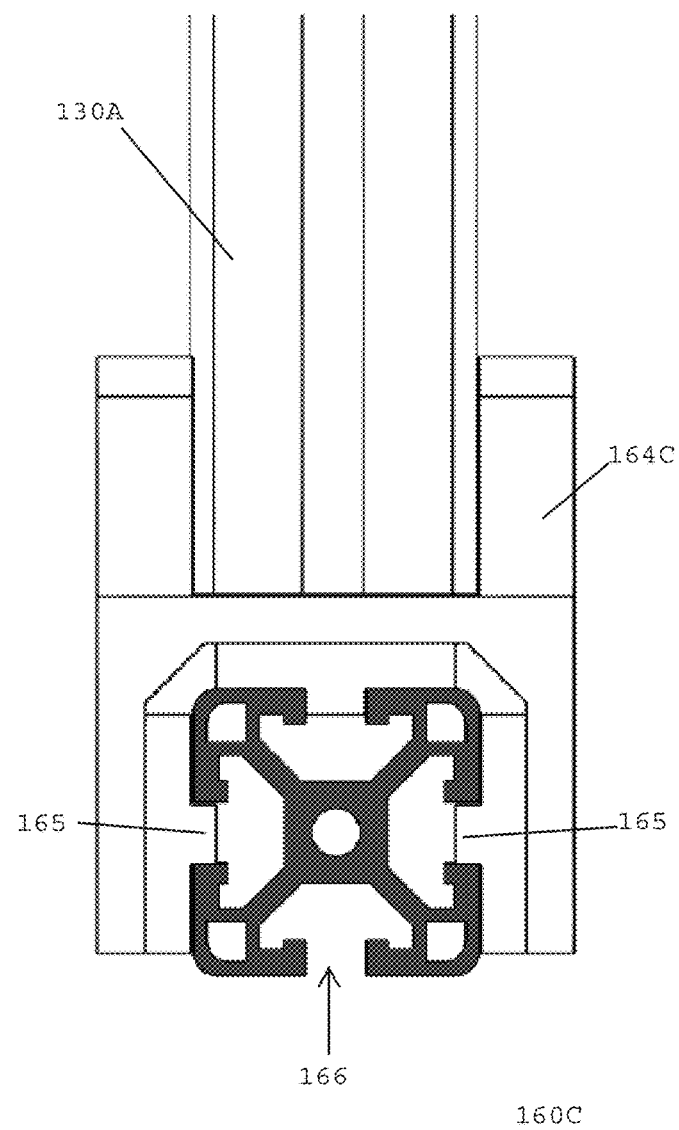
FIG. 5A
FIG. 5B

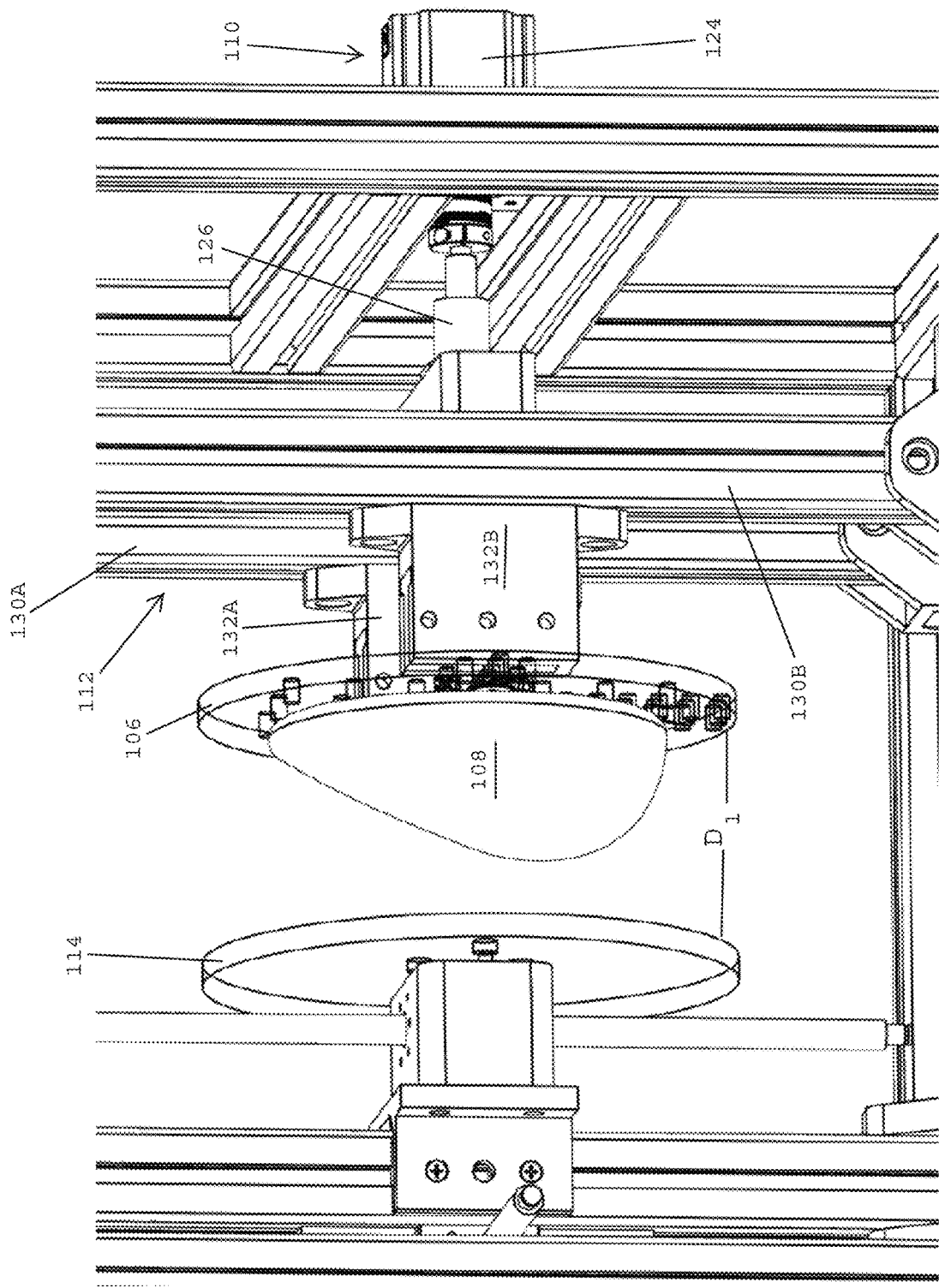

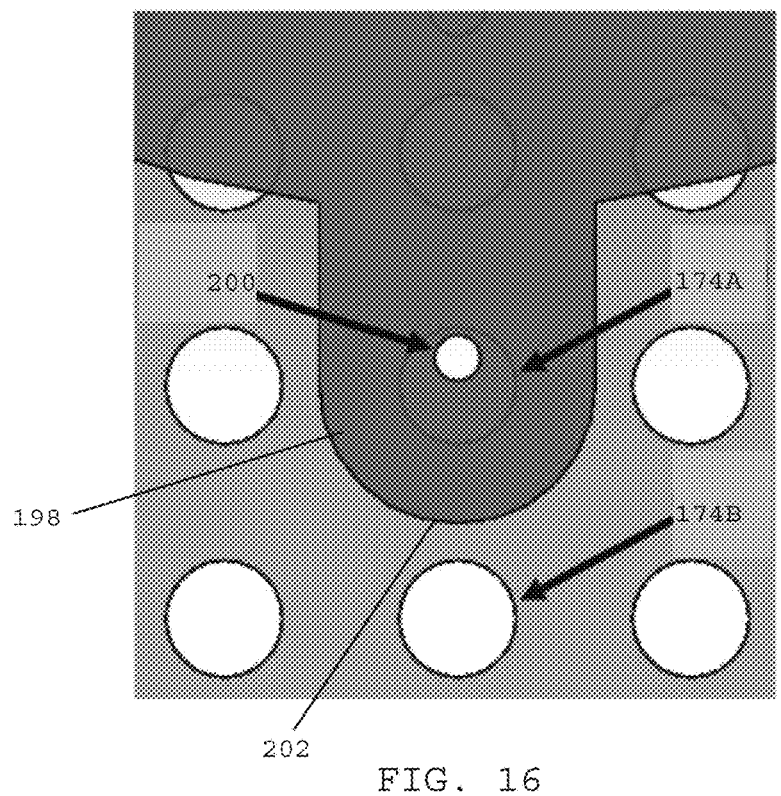
FIG. 16
FIG. 17
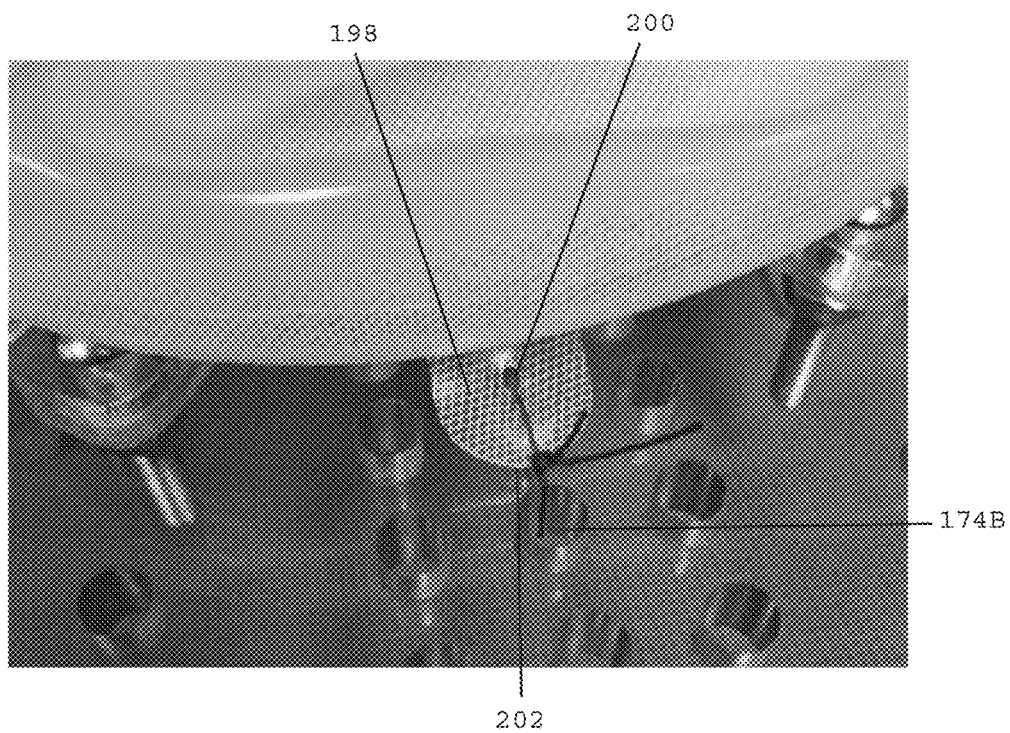

TESTING SYSTEMS, FIXTURES AND METHODS FOR MECHANICALLY TESTING IMPLANTS INCLUDING BREAST TISSUE EXPANDERS

BACKGROUND OF THE INVENTION

Field of the Invention

The present patent application is related to implants, and is more specifically related to systems, devices, and methods for mechanically testing implants, such as breast tissue expanders.

Description of the Related Art

Many of the current test methods detailed in international standards, such as ASTM F1441 or ISO 14607, to characterize the mechanical performance of breast tissue expanders were originally designed to evaluate breast implants and were adopted for breast tissue expanders. These test methods, however, do not fully represent the clinical environment in which breast tissue expanders are used, namely, the fact that breast tissue expanders have suture tabs that are used to fixate the device within the breast pocket. In addition, the existing test methods only stress the expanders in one or two directions, but it is still well known that clinically breast tissue expanders are stressed in all three directions of three-dimensional space. Thus, there is a need to develop an advanced test method that more accurately represents the clinical use and loading conditions of a breast tissue expander device.

In view of the above-noted deficiencies, there remains a need for test fixtures and testing methods that apply stress to breast implants in all directions of a three dimensional space. There also remains a need for test fixtures and testing methods that enable the suture tabs of the expander to be fixated and under constant tension. In addition, there remains a need for test fixtures that enable operators to have complete custom control of the test parameters and movements of base plates that hold the breast implants, as well as the opposing compression plates that apply compression and stress forces on the breast implants.

SUMMARY OF THE INVENTION

In one embodiment, a test fixture is used for accurately evaluating the mechanical performance of implants, such as breast tissue expanders. The test fixture is configured to stress the shell to suture tab interface of the breast tissue expanders in a cyclic manner to mimic the dynamic loading conditions that would be seen clinically. In one embodiment, the test fixture is designed to apply shear loads both horizontally (x-direction) and vertically (y-direction) as well as compressive loads (z-direction), thus achieving load in all directions of a three-dimensional space.

In one embodiment, the test fixture includes a frame (e.g., a rigid frame), a base plate to which the breast tissue expander is fixated, and a compression plate which opposes the base plate for compressing the breast tissue expander.

In one embodiment, the base plate is able to move forward and back in the Z-direction to achieve various levels of compression.

In one embodiment, the compression plate is able to move horizontally in the X-direction and vertically in the Y-direction to apply shear loads on the implant. The horizontal and vertical movement of the compression plate are independent of each other, which allows for full 360 degrees movement of the compression plate, if desired.

In one embodiment, the base plate is able to move in all three of the above-described axial directions. For example, in one embodiment, the base plate is able to: 1) move forward and back in the Z-direction to achieve various levels of compression, 2) move horizontally in the X-direction to apply shear loads on the implant, and 3) move vertically in the Y-direction to apply shear loads on the implant.

In one embodiment, the compression plate is able to move in all three of the alcove-described axial directions. For example, in one embodiment, the base plate is able to: 1) move forward and back in the Z-direction to achieve various levels of compression, 2) move horizontally in the X-direction to apply shear loads on the implant, and 3) move vertically in the Y-direction to apply shear loads on the implant.

In one embodiment, both the base plate and the compression plate are able to move independently of one another in all three of the above-described axial directions (i.e., the Z-direction, the X-direction, and the Y-direction).

In one embodiment, sutures (of diverse sizes and types) may be used for securing the suture tabs of the implant to the base plate. In one embodiment, an intermediate chest wall plate is preferably placed between the base plate and implant device to cause the shell of the implant to protrude forward (toward the opposing compression plate), resulting in additional tension being placed on the suture tabs. The base plate may then be moved forward or back to achieve a desired level of compression, either based on the plate displacement or load cell feedback.

In one embodiment, upon commencing a mechanical test of the implant, the compression plate moves horizontally and vertically repeatedly to apply shear loads to the tissue expander device. The logic of the test fixture is controlled using a custom LabView program, allowing the user to control test parameters including compression depth, the horizontal and vertical displacement of the compression plate, the velocity and acceleration of the compression plate, and the movement pattern of the compression plate. In one embodiment, the test fixture may be operated until a desired number of cycles are completed, a failure occurs whereby the device ruptures at the shell to suture tab interface, or the suture tab delaminates from the rest of the tissue expander device.

The test fixture and testing methods disclosed herein apply stress to the breast implant in all directions of a three dimensional space, whereby the suture tabs of the expander are fixated and are in constant tension, and the user has complete custom control of the test parameters and movements of the base plate and compression plates.

In one embodiment, a test fixture for mechanically testing breast implants preferably includes a frame, a base plate coupled with the frame, and a first actuator coupled with the base plate for providing reciprocating motion to the base plate along a first axis.

In one embodiment, the test fixture preferably includes a compression plate coupled with the frame and opposing the base plate, a second actuator coupled with the compression plate for providing reciprocating motion to the compression plate along a second axis that intersects the first axis, and a third actuator coupled with the compression plate for providing reciprocating motion to the compression plate along a third axis that intersects both the first axis and the second axis In one embodiment, the test fixture desirably includes a control system in communication with the first, second, and third actuators for controlling the movement of the base plate along the first axis and the movement of the compression plate along the second and third axes.

In one embodiment, the first actuator is configured for changing a distance between the base plate and the compression plate as the base plate moves along the first axis.

In one embodiment, the first actuator preferably includes a first stepper motor that is in communication with the control system, and a first externally threaded rod being coupled with the first stepper motor and the base plate for guiding the reciprocating motion of the base plate along the first axis.

In one embodiment, the base plate has a first major surface, and the compression plate has a major surface that directly opposes the first major surface of the base plate.

In one embodiment, the first major surface of the base plate lies in a first plane and the major surface of the compression plate lies in a second plane that is parallel with the first plane.

In one embodiment, the base plate preferably has two or more fixation points accessible at the first major surface of the base plate that are configured for securing a breast implant over the first major surface of the base plate.

The two or more fixation points may include two of more openings formed in the base plate and/or two or more protrusions projecting from the first major surface of the base plate.

In one embodiment, the second actuator desirably includes a second stepper motor that is in communication with the control system, and a second externally threaded rod being coupled with the second stepper motor and the compression plate for guiding reciprocating motion of the compression plate along the second axis.

In one embodiment, the third actuator desirably includes a third stepper motor that is in communication with the control system, and a third externally threaded rod extending being coupled with the third stepper motor and the compression plate for guiding reciprocating motion of the compression plate along the third axis.

In one embodiment, the control system preferably includes a program (e.g., software) for dynamically varying a distance between the base plate and the compression plate.

In one embodiment, the control system may include a program (e.g., software) for dynamically varying the relative horizontal (e.g., the second axis $A_2$) and vertical positions (e.g., the third axis $A_3$) of the compression plate relative to the base plate.

In one embodiment, a breast implant may be secured over a first major surface of the base plate. In one embodiment, the breast implant preferably has suture tabs and suture material may be used for securing the suture tabs to the base plate.

In one embodiment, a chest wall plate may be disposed between the first major surface of the base plate and a posterior surface of the breast implant. In one embodiment, the chest wall plate preferably projects toward the compression plate that opposes the base plate.

In one embodiment, the chest wall plate has a shape that simulates and/or replicates the anatomy of a patient, thereby generating additional tension on the suture tabs of the breast implant and the suture material that is utilized for securing the suture tabs to the base plate.

In one embodiment, the base plate has a central axis, and the control system is preferably configured for rotating the base plate around the central axis thereof.

In one embodiment, the compression plate has a central axis, and the control system is configured for rotating the compression plate around the central axis thereof.

In one embodiment, the first axis preferably defines the Z-axis coordinate of a Cartesian coordinate system for a three-dimensional space, the second axis preferably defines the X-axis coordinate of the Cartesian coordinate system for the three-dimensional space, and the third axis preferably defines the Y-axis coordinate of the Cartesian coordinate system for the three-dimensional space.

In one embodiment, a test fixture for mechanically testing breast implants desirably includes a frame, a base plate coupled with the frame, and a compression plate coupled with the frame and opposing the base plate.

In one embodiment, the test fixture desirably includes a control system in communication with the base plate and the compression plate. In one embodiment, the control system is preferably configured for providing reciprocating motion to the base plate along a first axis, reciprocating motion to the compression plate along a second axis that intersects the first axis, and reciprocating motion to the compression plate along a third axis that intersects both the first axis and the second axis.

In one embodiment, the control system desirably includes a first actuator in communication with the control system, the first actuator being coupled with the base plate for providing the reciprocating motion to the base plate along the first axis.

In one embodiment, the control system desirably includes a second actuator in communication with the control system, the second actuator being coupled with the compression plate for providing the reciprocating motion to the compression plate along the second axis that intersects the first axis.

In one embodiment, the control system desirably includes a third actuator in communication with the control system, the third actuator being coupled with the compression plate for providing reciprocating motion to the compression plate along a third axis that intersects both the first axis and the second axis.

In one embodiment, the control system may include a program that is in communication with the first actuator for dynamically varying the distance between the base plate and the compression plate along the first axis.

In one embodiment, a breast implant may be secured over a first major surface of the base plate.

In one embodiment, a chest wall plate may be disposed between the first major surface of the base plate and a posterior surface of the breast implant. The chest wall plate preferably projects toward the compression plate that opposes the base plate.

These and other preferred embodiments of the present patent application will be described in more detail herein.

BRIEF DESCRIPTION OF THE DRAWINGS

FIG. 28 is a cross-sectional view of the frame member shown in FIG. 2A.

FIG. 5A is an exploded view of a lower end of a vertically extending support bar, a lower guide bracket, and a lower guiderail of the first guide assembly shown in FIGS. 3A and 3B.

FIG. 5B shows the lower end of the vertically extending support bar, the lower guide bracket, and the lower guiderail of FIG. 5A after the components have been assembled together.

FIG. 6 is a side view of a first actuator and a first guide assembly of a test fixture, in accordance with one embodiment of the present patent application.

FIG. 16 a schematic view of a first stage of a method of securing a suture tab of a breast implant to a base plate of a test fixture, in accordance with one embodiment of the present patent application.

FIG. 17 shows the suture tab of FIG. 16 after the first stage of the method illustrated in FIG. 16 has been completed.

DETAILED DESCRIPTION OF PREFERRED EMBODIMENTS

Figure 1A:
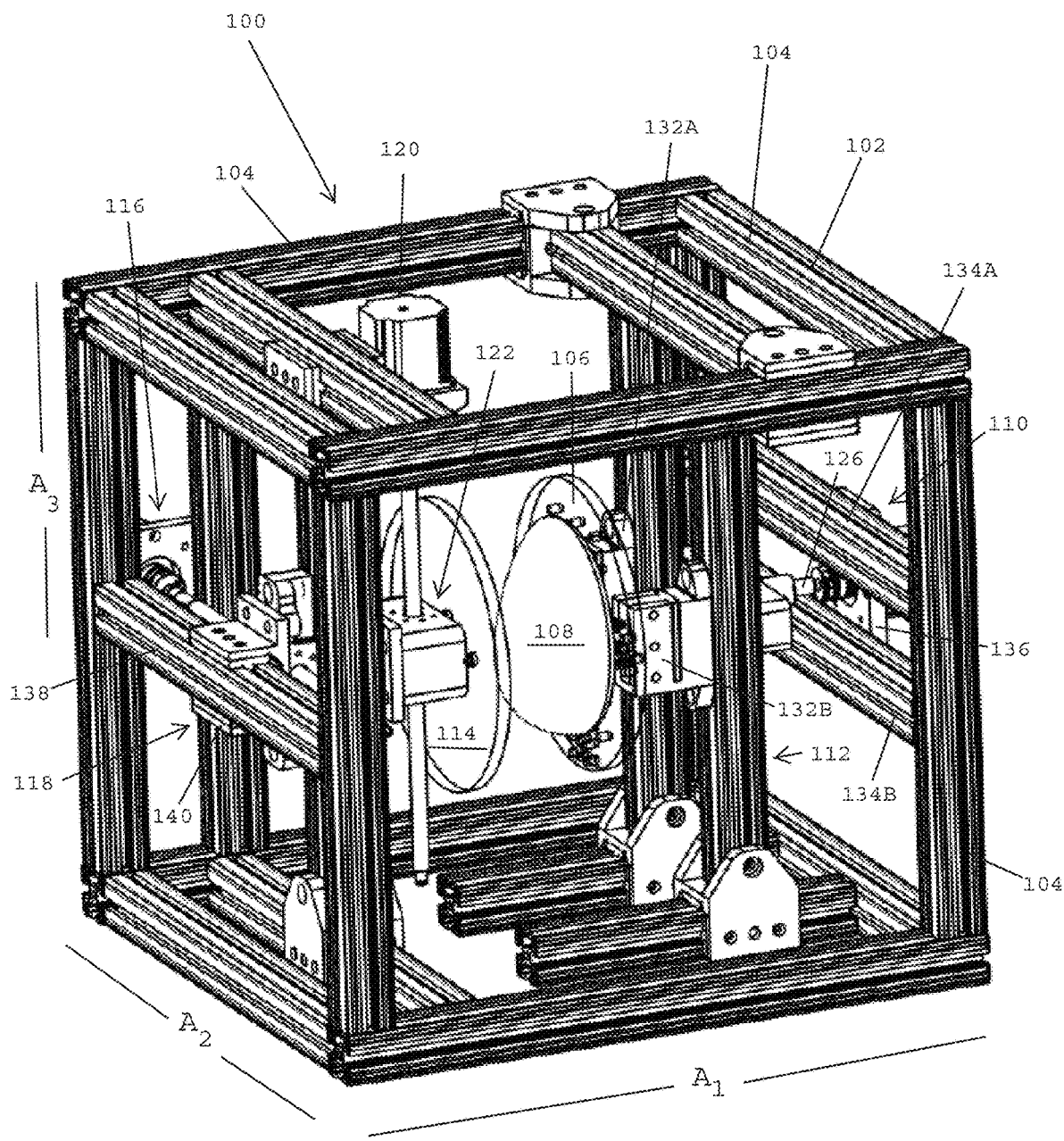
FIG. 1A is a perspective view of a front side of a test fixture configured for mechanically evaluating a breast implant, in accordance with one embodiment of the present patent application.
Figure 1B:
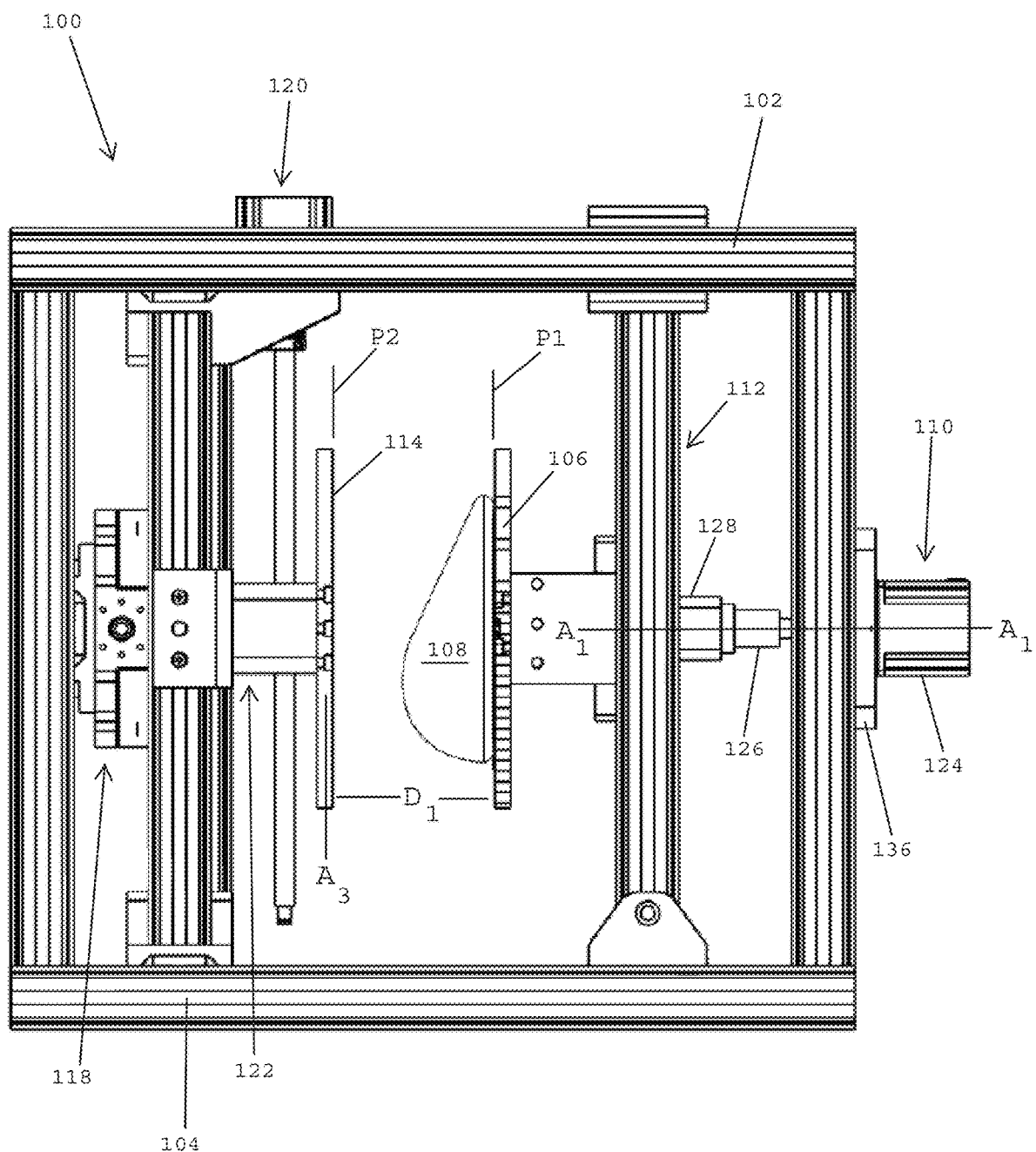
FIG. 1B is a front elevation view of the test fixture shown FIG. 1A.
Figure 1C:
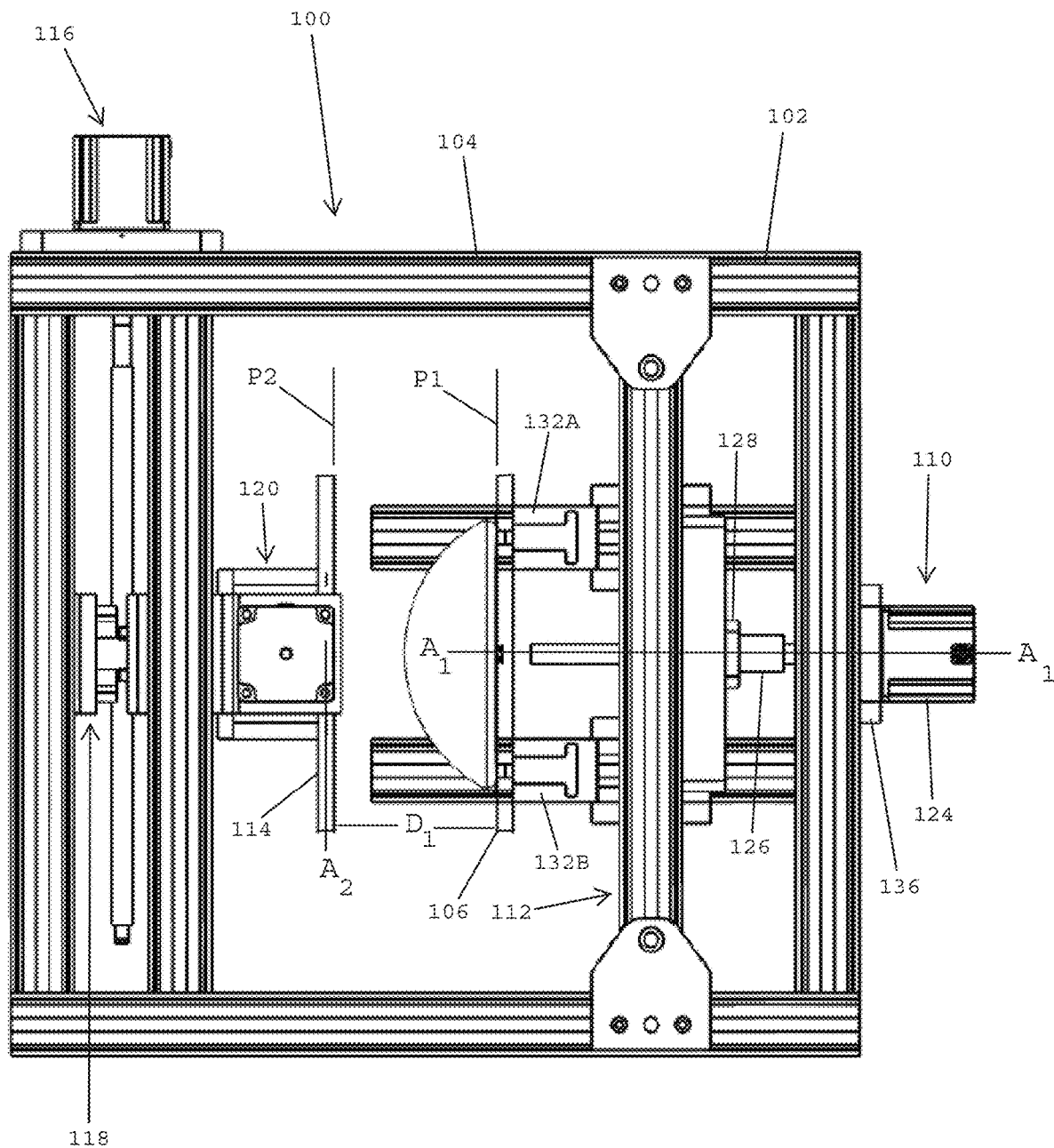
FIG. 1C is a top view of the test fixture shown in FIGS. 1A and 1B.

Referring to FIGS. 1A-1C, in one embodiment, a test fixture 100 for mechanically testing implants, such as breast implants (e.g., breast tissue expanders), preferably includes a frame 102 having a plurality of frame members 104 that are connected together to form the fame. In one embodiment, the frame 102 may have a cage or box-like structure. In one embodiment, one or more of the frame members 104 may also be configured to serves as guide rails for guiding movement of one or more components of the test fixture as will be described in more detail below.

In one embodiment, the frame members 104 may be fixed to one another to enhance the stability and structural integrity of the test fixture 100. In one embodiment, brackets (e.g., off the shelf brackets) may be used for securing the frame members 104 to one another. For example, the test fixture may have a box-like structure with a total of eight corners, and the frame members 104 at each of the eight corners may be joined to one another using brackets. In one embodiment, the brackets may be affixed to the frame members using fasteners (e.g., screws; threaded rods).

In one embodiment, the frame members 104 utilized to construct the test fixture 100 may be machined (e.g., have fastener openings formed therein) and fastening components such as threaded fasteners, screws, rods, threaded rods, nuts and bolts, may be used for holding the frame members 104 together to assemble the test fixture. In one embodiment, the frame members 104 may be welded together to form the test fixture. In one embodiment, the structure used to affix the frame members together may be located near or at the outer ends of the frame members.

In one embodiment, the test fixture 100 preferably includes a base plate 106 that is configured for securing a breast implant 108 thereto, whereupon the breast implant may be mechanically tested by operating the test fixture 100.

In one embodiment, the test fixture 100 preferably includes a first actuator 110 that is adapted to provide reciprocating motion to the base plate 106 along a first axis $A_1$ (FIGS. 1A and 1B). The first actuator 110 preferably includes a first guide assembly 112 that is coupled with the base plate 106 for guiding the reciprocating motion of the base plate along the first axis $A_1$. As used herein, the first axis $A_1$ may also be referred to as the Z axis or the Z direction.

In one embodiment, the test fixture 100 preferably includes a compression plate 114 that directly opposes the base plate 106. In one embodiment, the test fixture 100 preferably includes a second actuator 116 that is coupled with the compression plate 114 for providing reciprocating motion of the compression plate 114 along a second axis $A_2$ (FIG. 1C) that intersects the first axis $A_1$. In one embodiment, the second actuator 116 preferably includes a second guide assembly 118 that guides the reciprocating motion of the compression plate 114 along the second axis $A_2$. As used herein, the second axis $A_2$ may also be referred to as the X axis or the X direction.

In one embodiment, the test fixture 100 preferably includes a third actuator 120 that preferably provides reciprocating motion to the compression plate 114 along a third axis $A_3$ (FIG. 1B) that intersects both the second axis $A_2$ (FIG. 1C) and the first axis $A_1$ (FIGS. 1B and 1C). In one embodiment, the third actuator 120 preferably includes a third guide assembly 122 that preferably guides the reciprocating motion of the compression plate 114 along the third axis $A_3$. As used herein, the third axis $A_3$ may also be referred to as the Y axis or the Y direction.

Referring to FIGS. 1B and 10, in one embodiment, the first actuator 110 is a preferably operated to provide reciprocating motion to the base plate 106 along the first axis $A_1$ (e.g., the Z direction). During the reciprocating motion of the base plate 106, a distance $D_1$ between the base plate 106 and the opposing compression plate 114 may be dynamically varied. In one embodiment, the first actuator 110 preferably includes a first stepper motor 124 that is preferably coupled with a first externally threaded rod 126 that extends along the first axis $A_1$.

In one embodiment, the first major surface of the base plate 106 lies in a first plane P1 and the major surface of the compression plate 114 lies in a second plane P2 that is parallel with the first plane P1.

Referring to FIGS. 1A-1D, the first externally threaded rod 126 desirably meshes with internal threads of the nut 128, which in turn, is coupled with a pair of vertically extending bars 130A, 130B of the first guide assembly 112. Base plate mounting brackets 132A, 132B (FIG. 1C) are utilized for securing the base plate 106 to the vertically extending bars 130A, 130B (FIG. 1D) of the first guide assembly 112.

In one embodiment, the first stepper motor 124 of the first actuator 110 may be operated for rotating the first externally threaded rod 126 (FIGS. 1A-1C) about its longitudinal axis, which, in turn, moves the components of the first guide assembly 112 along the first axis $A_1$ (FIGS. 1B and 1C). Referring to FIGS. 1A and 1B, during the rotation of the first externally threaded rod 126, the distance $D_1$ between the opposing major faces of the base plate 106 and the compression plate 114 may be modified. In one embodiment, the first stepper motor 124 may change the direction of rotation of the first externally threaded rod 126 for providing reciprocating movement of the base plate 106 along the first axis $A_1$ (FIGS. 1B and 1C).

Figure 1D:
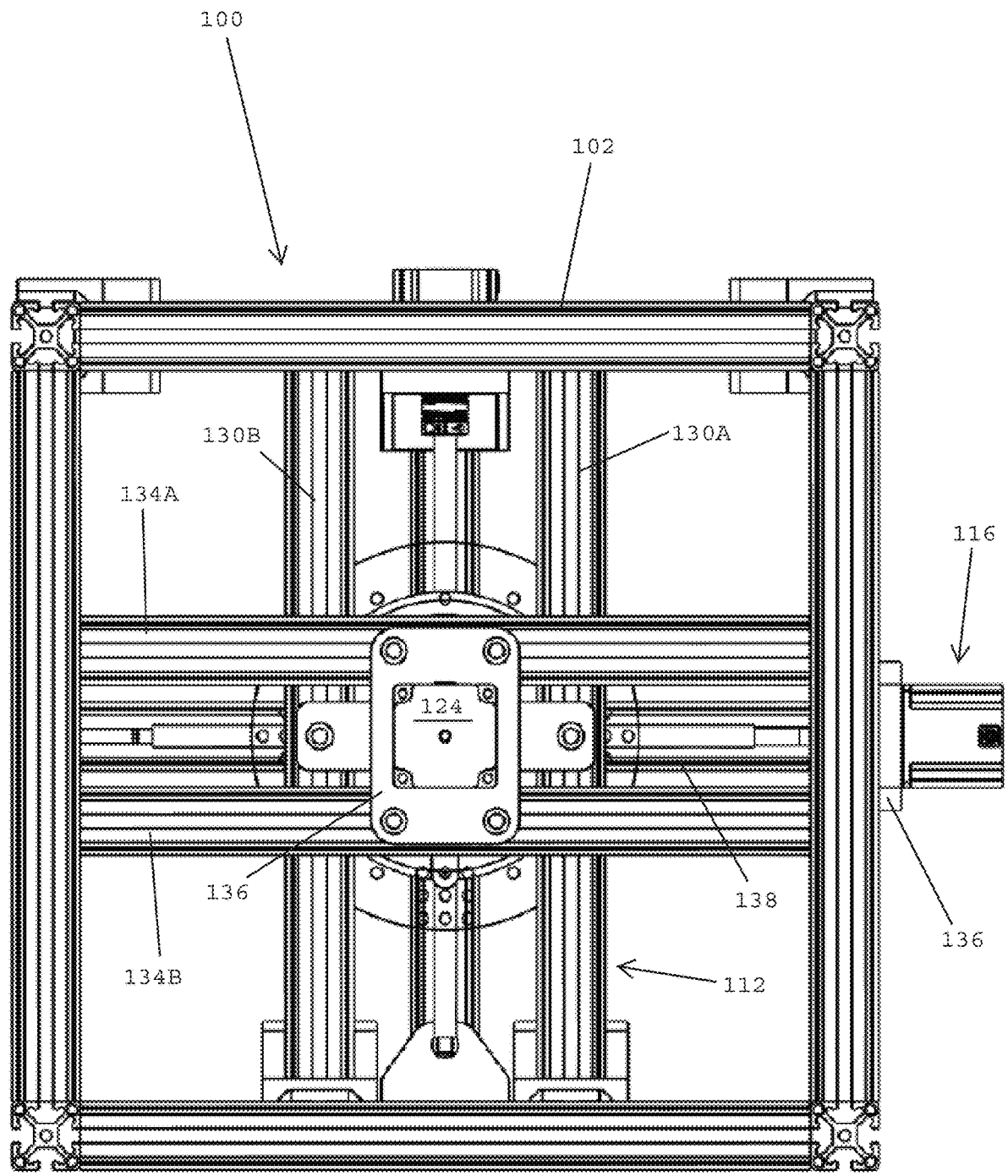
FIG. 1D is a proximal end view of the test fixture shown in FIGS. 1A-1C.

Referring to FIGS. 1A-1D, in one embodiment, the first stepper motor 124 of the first actuator 110 is mounted to horizontally extending frame members 134A, 134B via a first stepper motor attachment plate 136. Referring to FIG. 1D, in one embodiment, the horizontally extending frame members 134A, 134B are part of the frame 102 and are preferably static (i.e., do not move). The first stepper motor 124 may be activated for moving the vertically extending beams 130A, 130B of the first guide assembly 112 back and forth along the first axis $A_1$ (FIGS. 1B and 1C) for providing reciprocating motion to the base plate 106 along the first axis $A_1$.

Referring to FIGS. 1A and 1C-1G, in one embodiment, the test fixture 100 preferably includes the second actuator 116 that is adapted to provide reciprocating motion to the compression plate 114 along the second axis $A_2$ (FIG. 1C), which may also be referred to as the X direction. In one embodiment, the compression plate 114 is coupled with the second guide assembly 118, which preferably includes a horizontally extending guiderail 138 and a horizontally extending guide bracket 140 that enables reciprocating motion of the compression plate 114 along the second axis $A_2$ (FIG. 1C). In one embodiment, the second actuator 116 preferably includes a second stepper motor 142 and a second externally threaded rod 144 that is coupled with the second stepper motor 142. In one embodiment, the second stepper motor 142 may be operated for rotating the second externally threaded rod 144 about its longitudinal axis, whereupon the external threads of the second externally threaded rod 144 engage with internal threads of the horizontally extending guide bracket 140 of the second guide assembly 118 for providing movement of the compression plate 114 along the second axis $A_2$ (FIG. 1C).

Figure 1E:
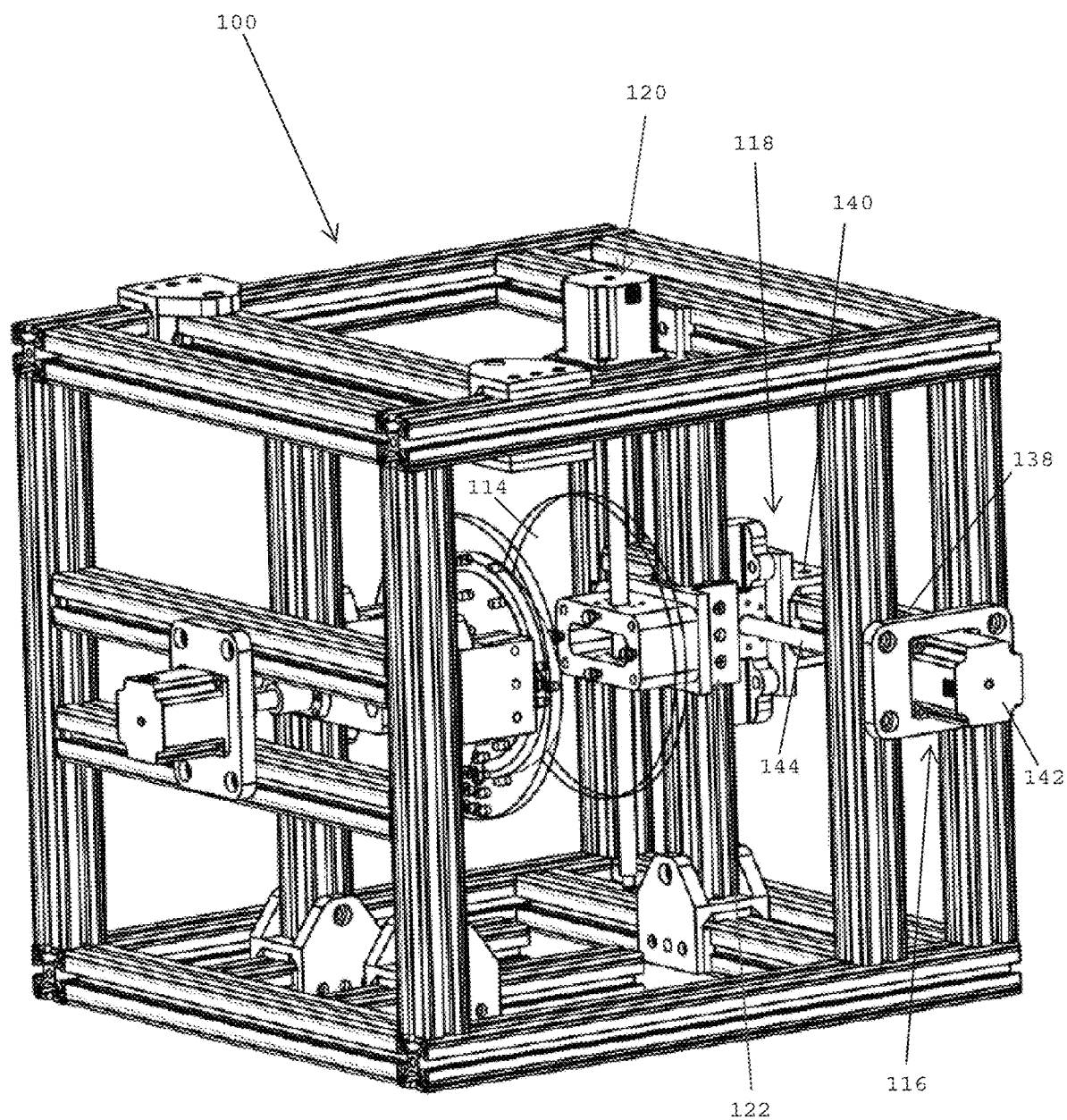
FIG. 1E is a perspective view of a rear side of the test fixture shown in FIGS. 1A-1D.
Figure 1F:
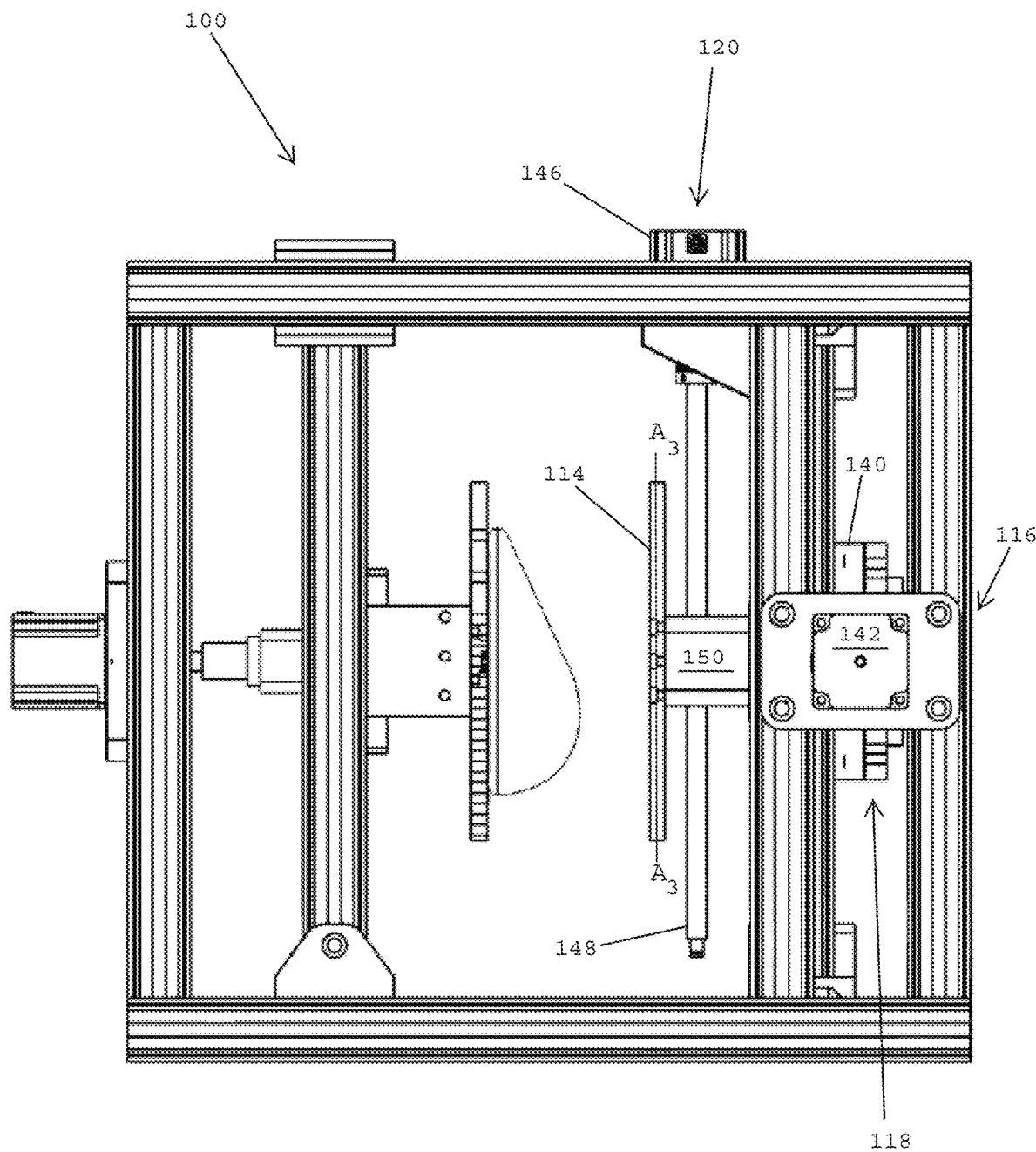
FIG. 1F is a rear elevational view of the test fixture shown in FIGS. 1A-1E.
Figure 1G:
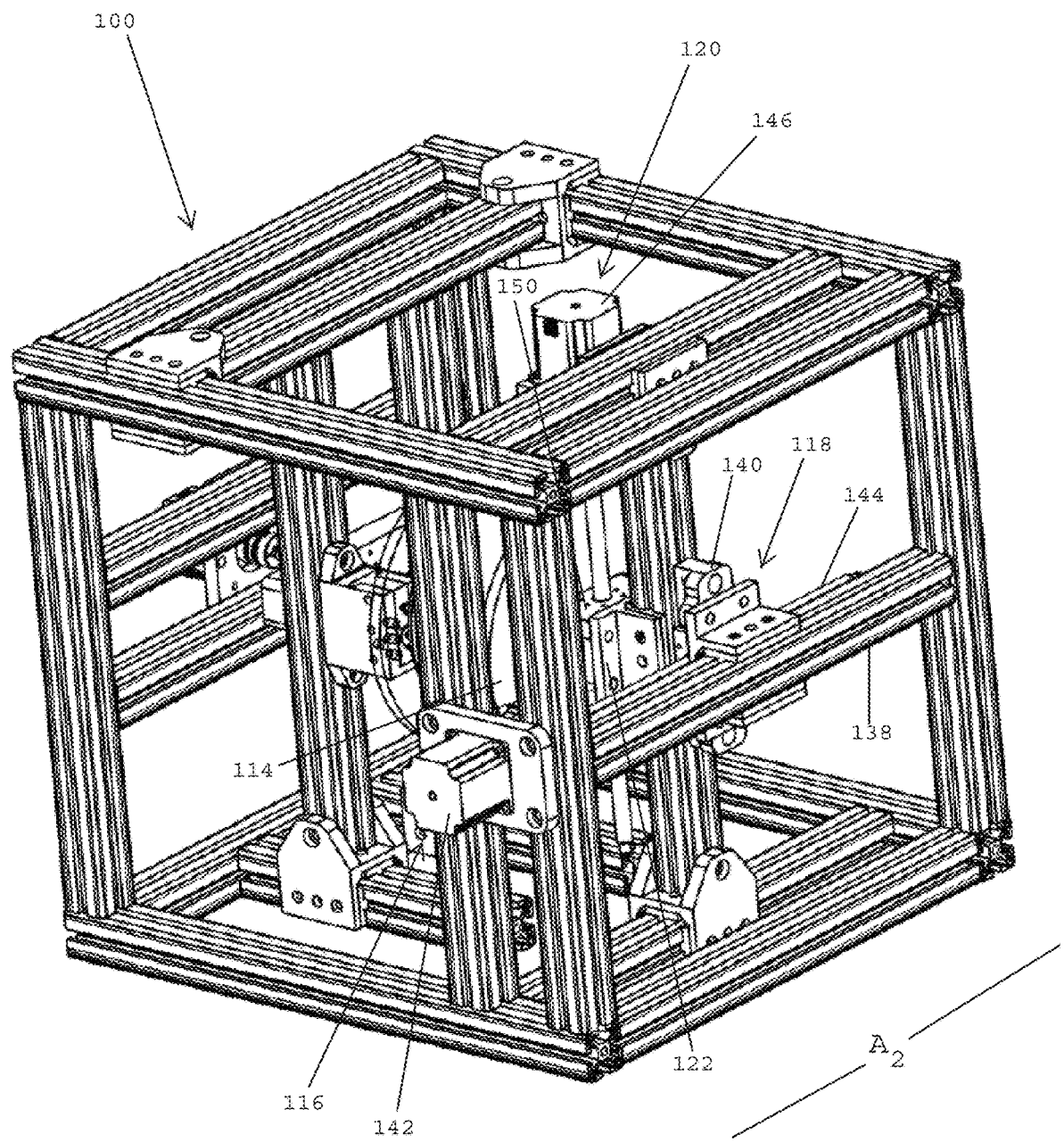
FIG. 1G is a perspective view of a distal end of the test fixture shown in FIGS. 1A-1F.

Referring to FIGS. 1E-1G, in one embodiment, the test fixture 100 preferably includes a third actuator 120 that preferably provides reciprocating motion to the compression plate 114 along a third axis $A_3$, which may also be referred to as the Y direction. In one embodiment, the third actuator 120 preferably includes a third stepper motor 146 and a third externally threaded rod 148 that is connected with the third stepper motor 146. In one embodiment, the external threads of the third externally threaded rod 148 preferably mesh with internal threads of a compression plate support bracket 150. In one embodiment, activation of the third stepper motor 146 preferably rotates the third externally threaded rod 148 about its longitudinal axis. As the third externally threaded rod 148 rotates about its longitudinal axis, the external threads of the third externally threaded rod mesh with the internal threads of the compression plate support bracket 150 for moving the compression plate support bracket 150 along the third axis $A_3$, which, in turn, provides motion to the compression plate 114 along the third axis $A_3$. In one embodiment, the third actuator 120 preferably includes the third guide assembly 122, which is configured to guide the reciprocating motion of the compression plate 114 along the third axis $A_3$.

Figure 2A:
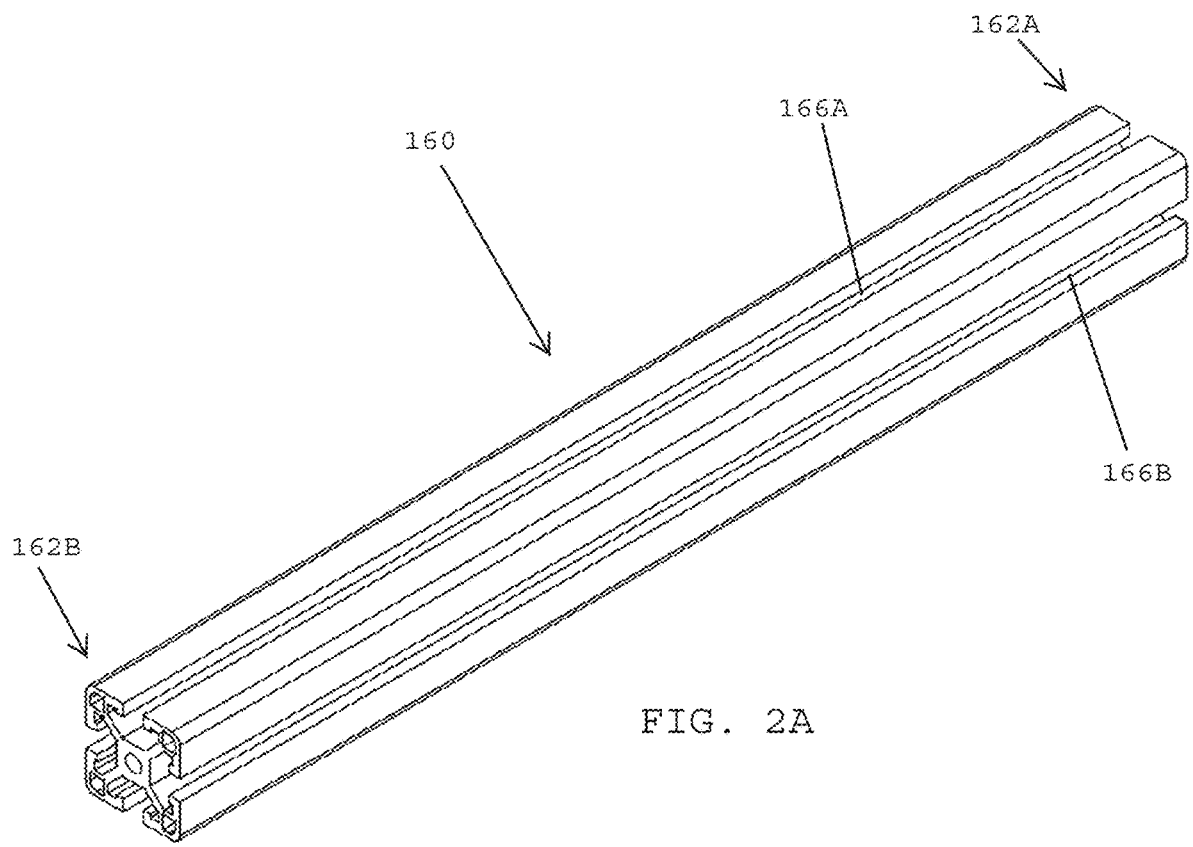
FIG. 2A is a perspective view of a frame member of the test fixture shown in FIG. 1A.
Figure 2B:
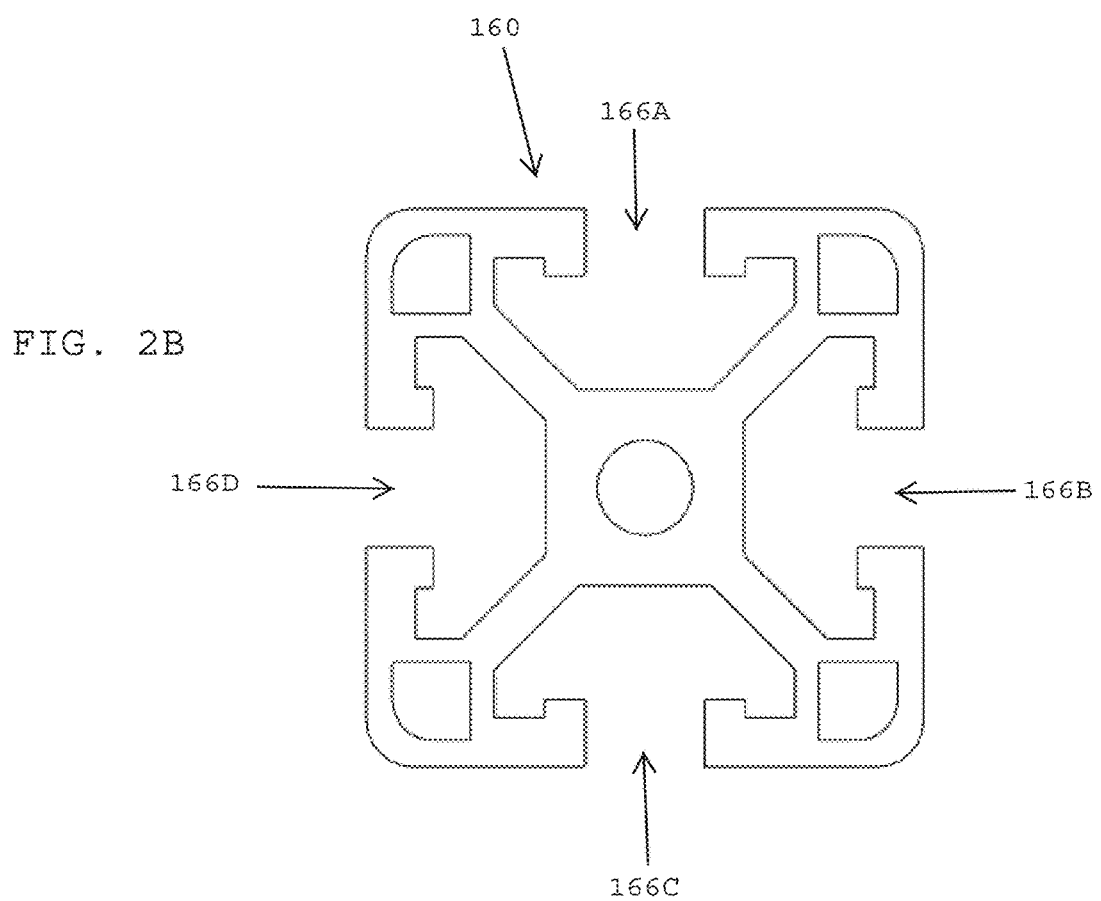
Figure 18:
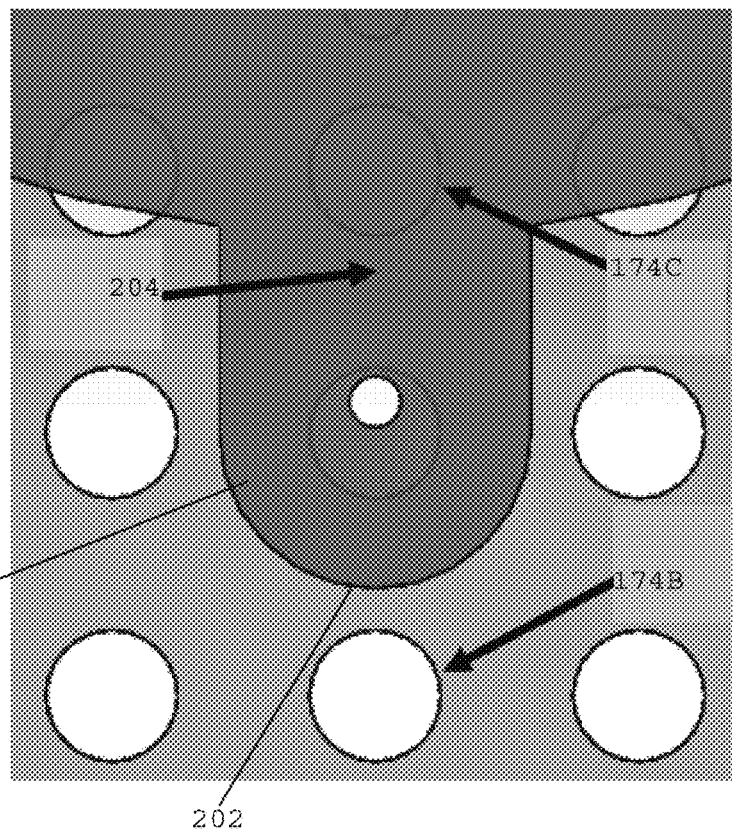
FIG. 18 is a schematic view of a second stage of a method of securing a suture tab of a breast implant to a base plate of a test fixture, in accordance with one embodiment of the present patent application.

Referring to FIGS. 1A, 2A and 2B, in one embodiment, the test fixture 100 (FIG. 1) preferably includes one or more guide rails 160 that are configured for guiding the reciprocating motion of the base plate 106 (FIG. 1) along the first axis $A_1$ (FIG. 1B), and/or the reciprocating motion of the compression plate 114 along the second axis $A_2$ (FIG. 1C) and/or the third axis $A_3$ (FIG. 18). One or more of the guide rails 160 may also be a frame member of the frame of the test fixture. In one embodiment, the guide rail 160 may be an extruded component (e.g., made of metal) having a proximal end 162A, a distal end 162B and a plurality of grooves 166A-166D that extend along the length of the guide rail 160 from the proximal end 162A to the distal end 162B thereof. In one embodiment, the guide rail 160 may be adapted to receive projections provided on guide brackets that are adapted to slide along the length of the guide rail 160 for supporting reciprocal motion of the base plate 106 and/or the compression plate 114 (FIG. 1).

Figure 3A:
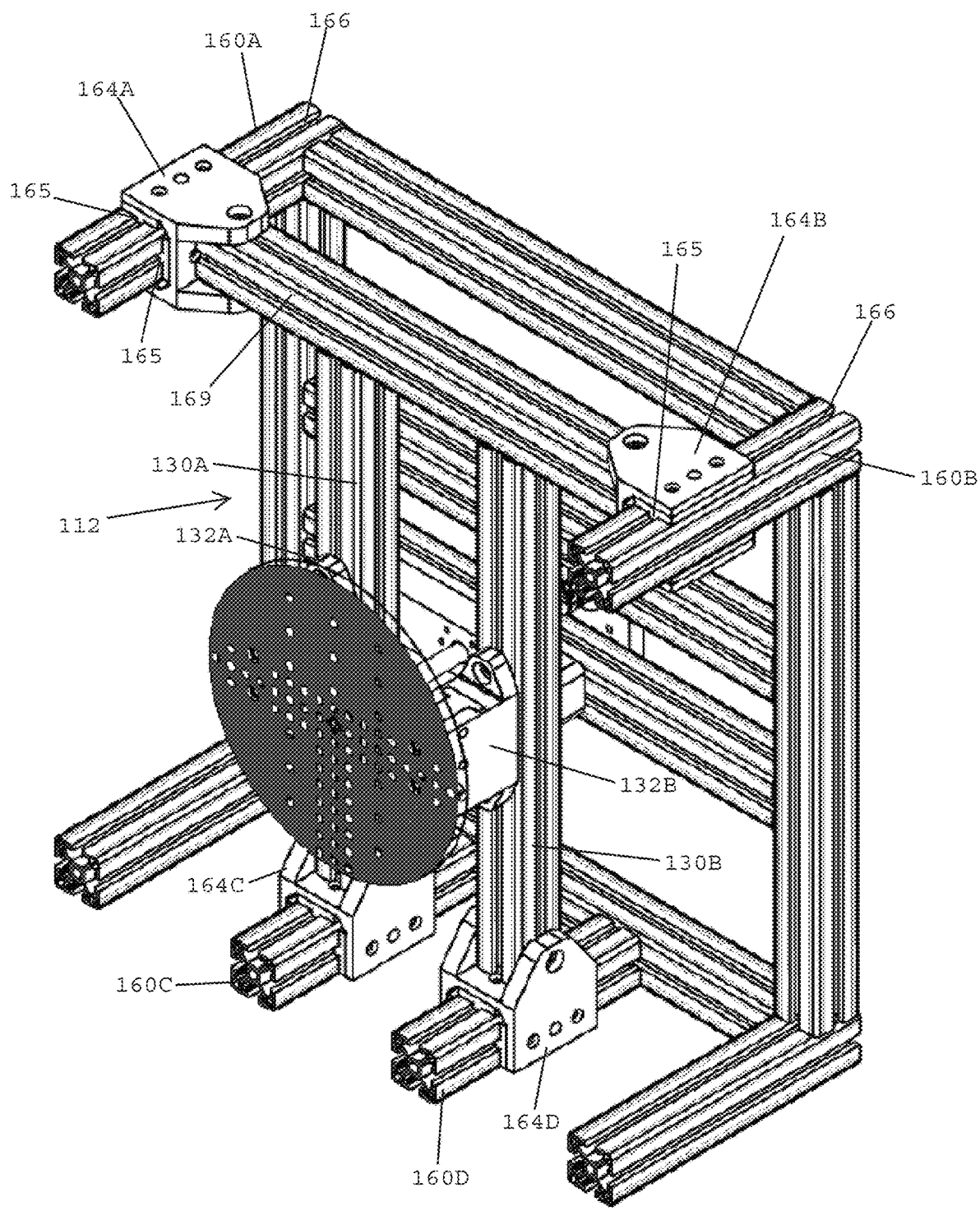
FIG. 3A is a perspective view of a first guide assembly of the test fixture shown in FIG. 1A.

Referring to FIGS. 3A and 38, in one embodiment, the first guide assembly 112 that is configured for guiding reciprocal motion of the base plate 106 along the first axis $A_1$ (FIG. 18) preferably includes first and second upper guide rails 160A, 160B that are located at an upper end of the first guide assembly 112. The first guide assembly 112 preferably includes a stabilizing bar 169 (e.g., a horizontally extending member) that is coupled with the first and second upper guide rails 160A, 160B by respective guide rail brackets 164A, 164B. The guide rail brackets 164A, 164B preferably include projections 165 that are seated within the elongated grooves 166 (FIG. 2A) of the first and second upper guide rails 160A, 160B for guiding the reciprocal movement (e.g., sliding movement) of the stabilizing bar 169 at the upper end of the first guide assembly 112.

In one embodiment, the first guide assembly 112 preferably includes first and second lower guiderails 160C, 160D that are preferably located at a lower end of the first guide assembly 112. The first guide assembly 112 preferably includes lower guide brackets 164C, 164D that are coupled with the first and second lower guiderails 160C, 160D for guiding reciprocating motion (e.g., sliding motion) of the first guide assembly 112 along the first axis $A_1$ (FIG. 1B). The first guide assembly 112 preferably includes the vertically extending support bars 130A, 130B having respective upper ends connected to the stabilizing bar 169 and lower ends connected to the respective lower guide rail brackets 164C, 164D. The first guide assembly 112 preferably includes base plate mounting brackets 132A, 132B (FIG. 3A) that secure the base plate 106 to the respective vertical support members 130A, 130B.

Figure 3B:
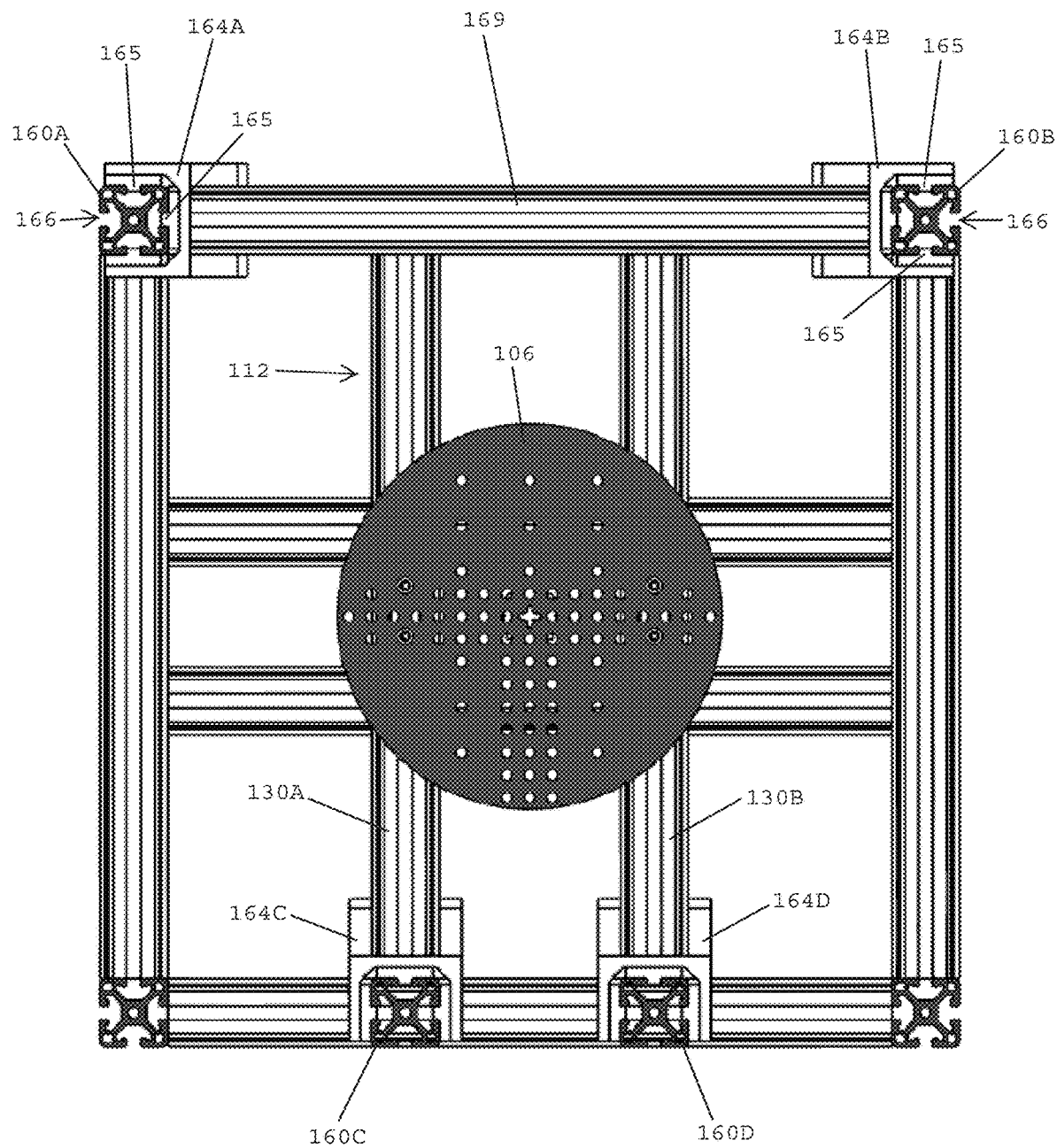
FIG. 3B is an elevation view of the first guide assembly shown in FIG. 3A.
Figure 4A:
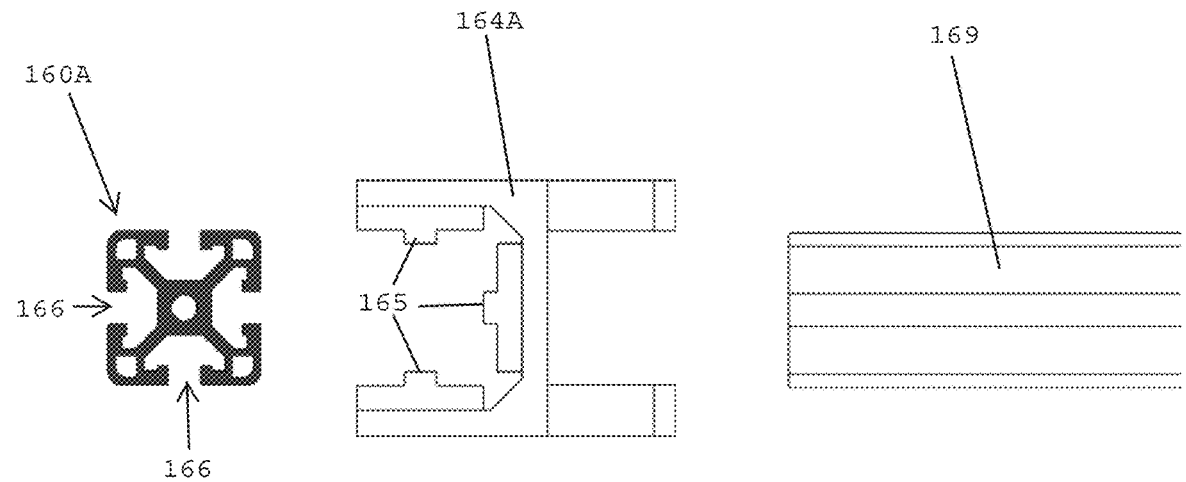
FIG. 4A is an exploded view of a guide rail, a guide rail bracket and a stabilizing bar of the first guide assembly shown in FIGS. 3A and 3B.
Figure 4B:
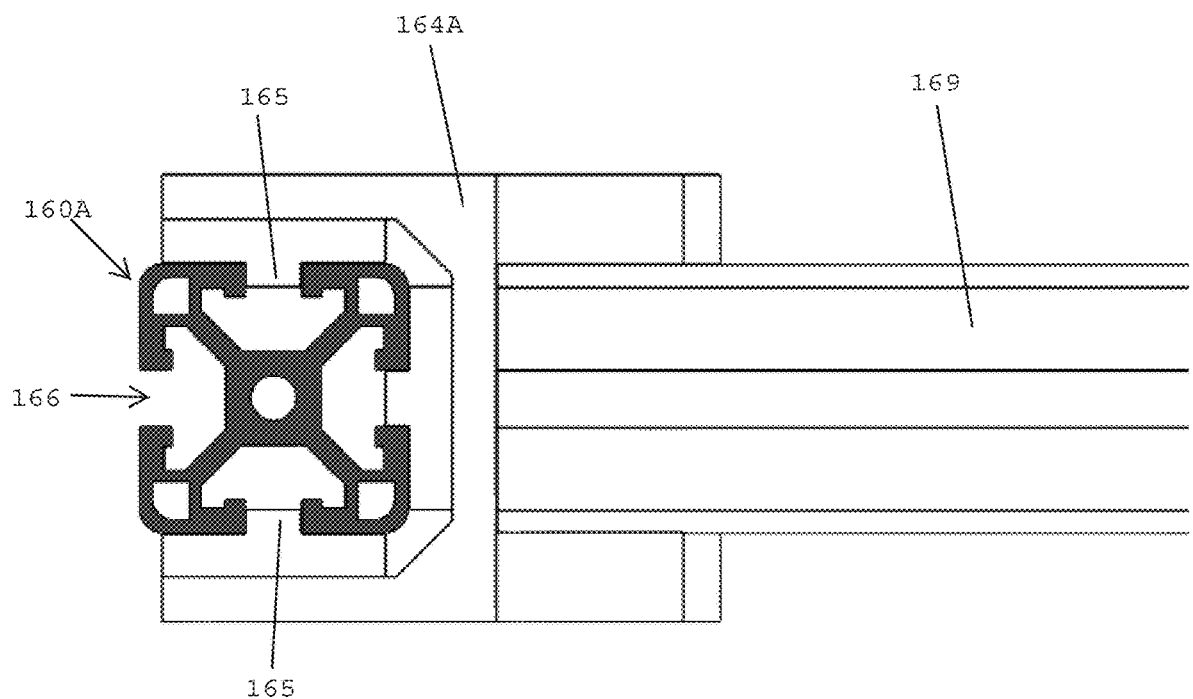
FIG. 4B shows the guide rail, the guide rail bracket and the stabilizing bar of FIG. 4A after the components have been assembled together.

Referring to FIGS. 4A and 4B, in one embodiment, the first upper guide rail 160A is preferably located at an upper end of the first guide assembly 112 (FIGS. 3A and 3B). The first upper guide rail 160A has a plurality of elongated groves 166 that extend along the length of the first upper guide rail. The first guide assembly preferably includes the first guide rail bracket 164A, which is utilized for connecting the stabilizing bar 169 with the first upper guide rail 160A. The first guide rail bracket 164A preferably includes projections 165 that are seated within the elongated grooves 166 of the first upper guide rail 160A for guiding the reciprocal movement (e.g., sliding movement) of the stabilizing bar 169 at the upper end of the first guide assembly 112.

Referring to FIGS. 5A and 5B, in one embodiment, the first guide assembly 112 preferably includes the first lower guide rail 160C, which is preferably located at the lower end of the first guide assembly 112 (FIGS. 3A and 3B). The first guide assembly 112 preferably includes the first lower guide bracket 164C that preferably interconnects the lower end of the first vertically extending support bar 130A with the first lower guide rail 160C. The first lower guide rail bracket 164C preferably includes projections 165 that are seated within the elongated grooves 166 of the first lower guide rail 160C for guiding the reciprocal movement (e.g., sliding movement) of the lower end of the first guide assembly 112 along the first axis $A_1$.

Figure 7:
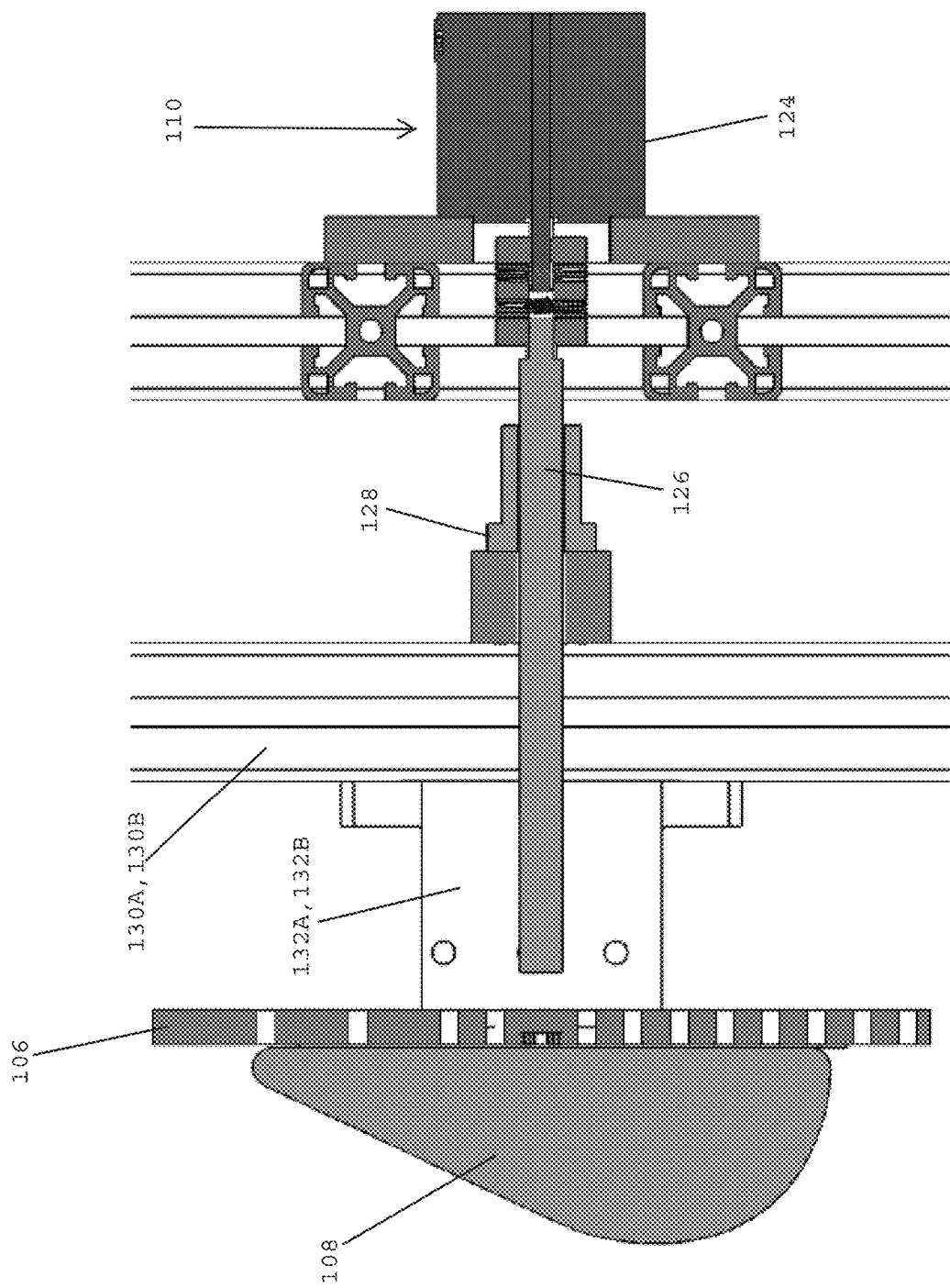
FIG. 7 is a cross-sectional view of the first actuator and the first guide assembly shown in FIG. 6.

Referring to FIGS. 6 and 7, in one embodiment, the first actuator 110 including the first stepper motor 124 is coupled with the first guide assembly 112 via the first externally threaded rod 126. Activating the first stepper motor 124 preferably rotates the first externally threaded rod 126 about its longitudinal axis for moving the first guide assembly 112 in a reciprocating pattern for varying the distance $D_1$ between the base plate 106 and the clamping plate 114 that directly opposes the base plate.

The base plate 106 is preferably mounted to the first and second vertical support bars 130A, 130B of the first guide assembly 112 via the respective base plate mounting brackets 130A, 130B.

In one embodiment, the first actuator 110 preferably includes the first stepper motor 124, the first externally threaded rod 126, and internally threaded nut 128 having internal threads that engage the external threads of the first externally threaded rod 126, and the base plate mounting brackets 132A, 132B that secure the base plate 106 to first and second vertically extending members 130A, 130B. In one embodiment, an implant 108 (e.g., a breast tissue expander) may be secured to a first major surface of the base plate 106, such as by using sutures. In one embodiment, activation of the first stepper motor 124 preferably rotates the first externally threaded rod 126 about its longitudinal axis which, in turn, engages with the internal threads of the nut 128 for moving the vertical members 130A, 130B of the first guide assembly 112, which in turn, moves the base plate 106 along the first axis $A_1$ (FIG. 1B).

In one embodiment, the first externally threaded rod 126 may be rotated about its longitudinal axis in a first direction for reducing the distance $D_1$ between the base plate 106 and the opposing compression plate 114. In one embodiment, the first externally threaded rod 126 may be rotated about its longitudinal axis in a second direction (i.e., opposite the first direction) for increasing the distance $D_1$ between the base plate 106 and the opposing compression plate 114.

Figure 8:
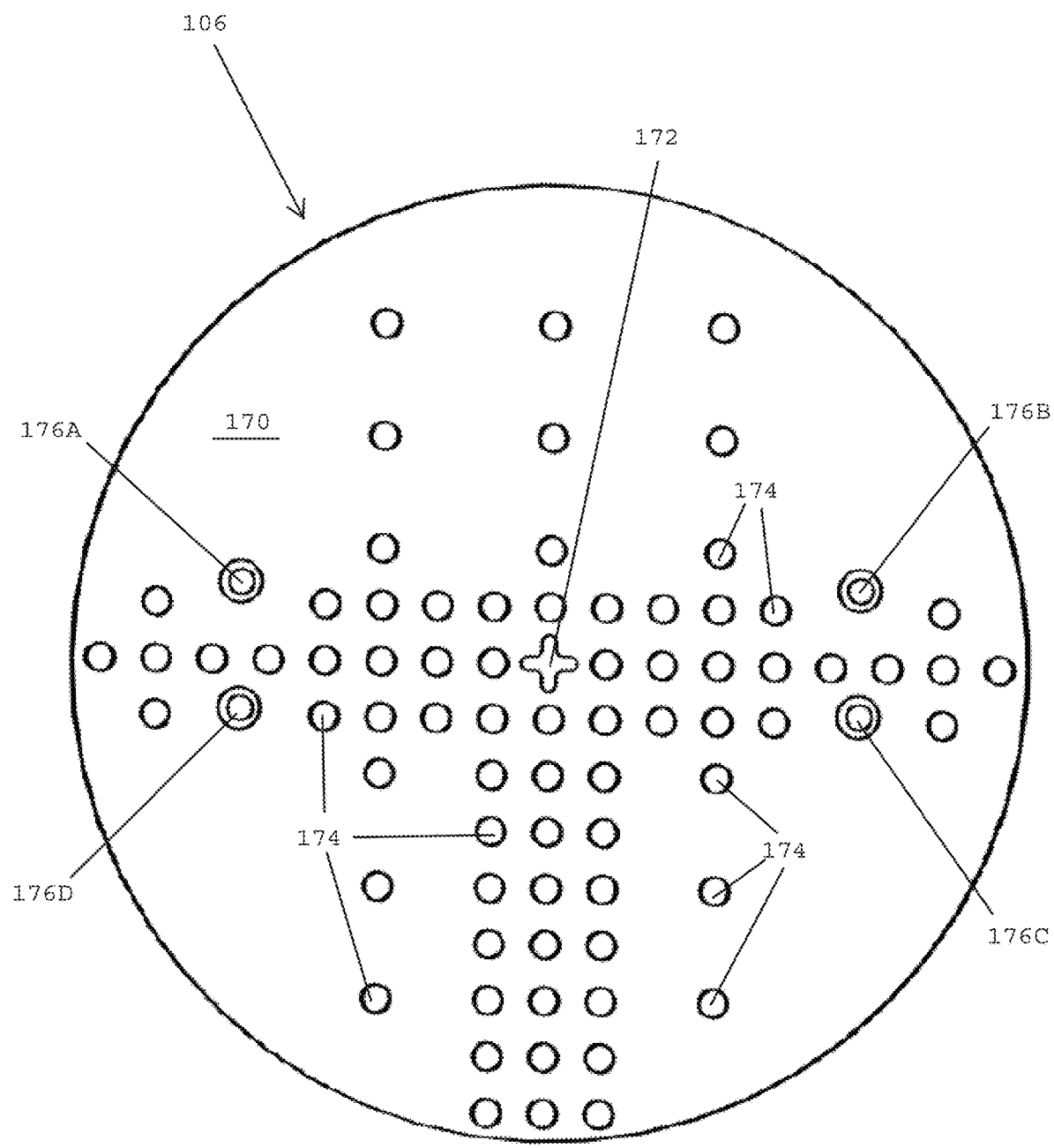
FIG. 8 is a front view of a first major surface of a base plate of a test fixture, in accordance with one embodiment of the present patent application.

Referring to FIG. 8, in one embodiment, the base plate 106 preferably has a first major surface 170 that directly opposes a major surface of the opposing compression plate 114 (FIG. 6). In one embodiment, the base plate 106 preferably has a centrally located opening 172 that preferably defines a center of the base plate 106. In one embodiment, the base plate desirably has a plurality of implant mounting openings 174 formed therein that are utilized to secure the implant 108 (FIG. 1A) over the first major surface 170 of the base plate 106. In one embodiment, the plurality of implant mounting openings 174 are configured to receive one or more sutures that may be passed through both the implant mounting openings and suture tabs of the implant for securing the implant over the first major surface 170 of the base plate 106.

Figure 9:
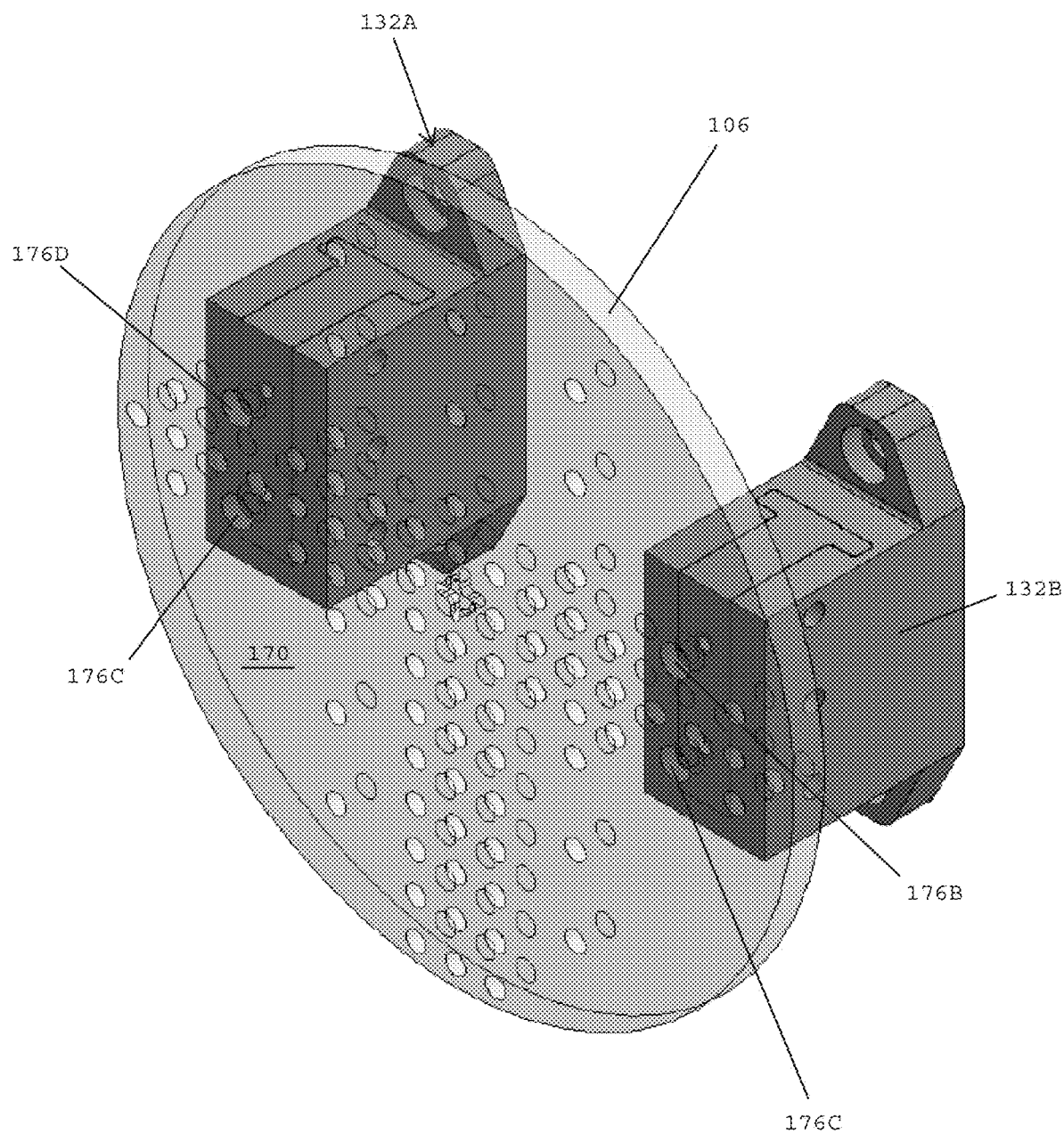
FIG. 9 is a perspective view of the base plate of FIG. 8 connected with base plate mounting brackets, in accordance with one embodiment of the present patent application.

Referring to FIGS. 8 and 9, in one embodiment, the base plate 106 preferably includes bracket mounting openings 176A-176D that are utilized for securing the base plate 106 to the base plate mounting brackets 132A, 132B (FIG. 6).

Referring to FIG. 9, in one embodiment, the base plate mounting brackets 132A, 132B are preferably aligned with the respective base plate mounting openings 176A-176D that pass through the base plate 106 for securing the base plate 106 to the base plate mounting brackets 132A, 132B. In one embodiment, the base plate mounting brackets 132A, 132B are preferably secured to the vertically extending support members 130A, 130B (FIGS. 3B and 6) of the first guide assembly 112 for securing the base plate 106 to the first guide assembly.

Figure 10A:
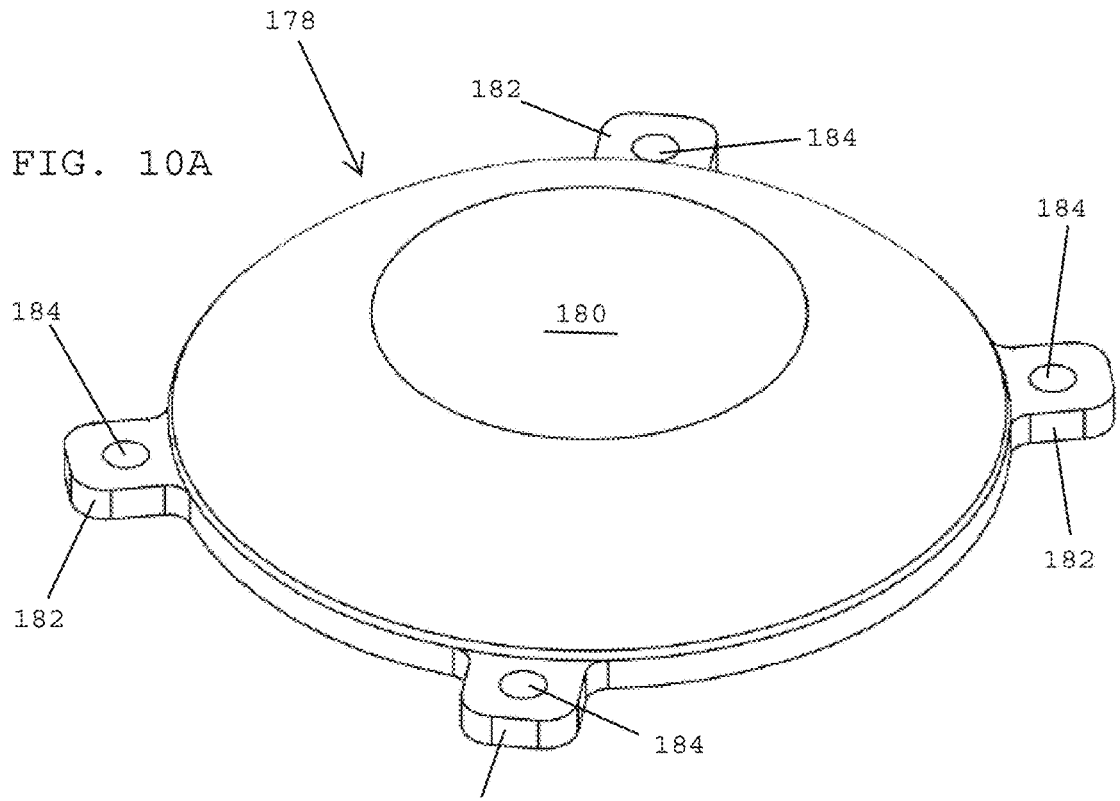
FIG. 10A is a perspective view of a chest wall plate adapted to be secured over the first major surface of the base plate shown in FIGS. 8 and 9, in accordance with one embodiment of the present patent application.
Figure 10B:
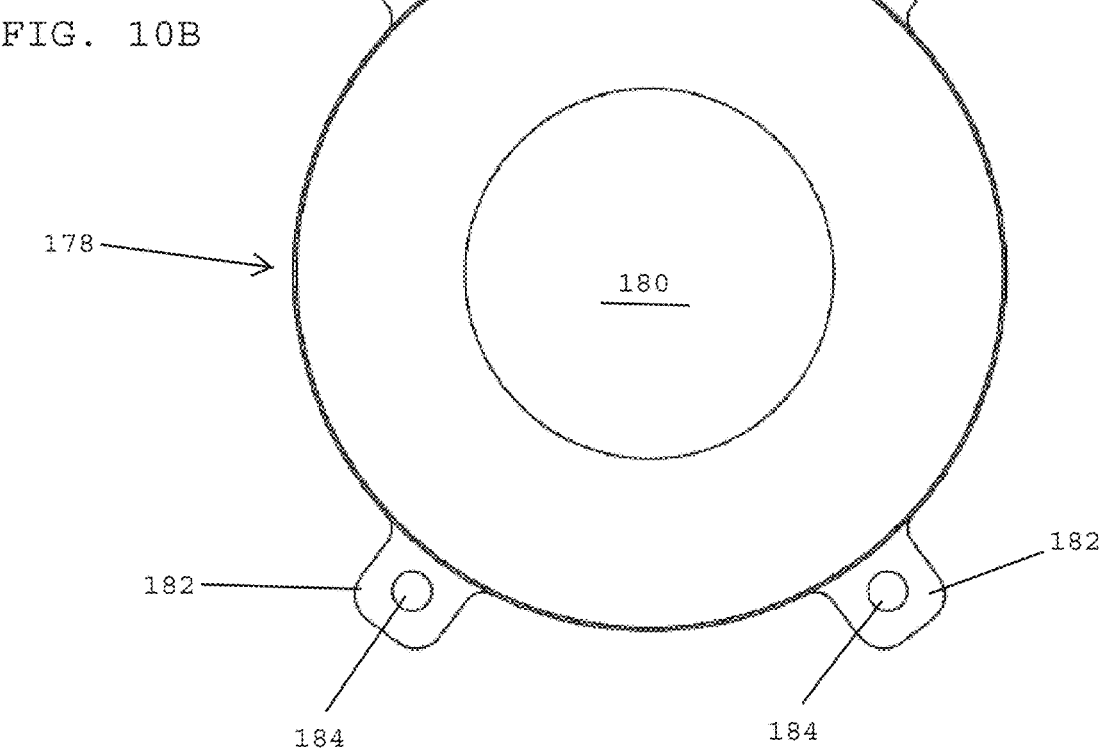
FIG. 10B is a top view of the chest wall plate shown in FIG. 10A.

Referring to FIGS. 10A and 10B, in one embodiment, the test fixture 100 (FIG. 1A) may include a chest wall plate 178 having a convexly curved dome 180 and securing tabs 182 having openings 184 that may be utilized for securing the chest wall plate 178 over the first major surface 170 of the base plate 106 (FIGS. 8 and 9). In one embodiment, the chest well plate 178 is preferably adapted to being positioned between the first major surface 170 of the base plate 106 (FIG. 9) and a posterior wall of an implant 108 (FIG. 1A) for mimicking the anatomy of a patient and forming extra tension on the suture tabs of the implant 108 (FIG. 1A) and the suture material utilized to secure the suture tabs of the implant to the base plate 106 (FIG. 9).

Figure 11:
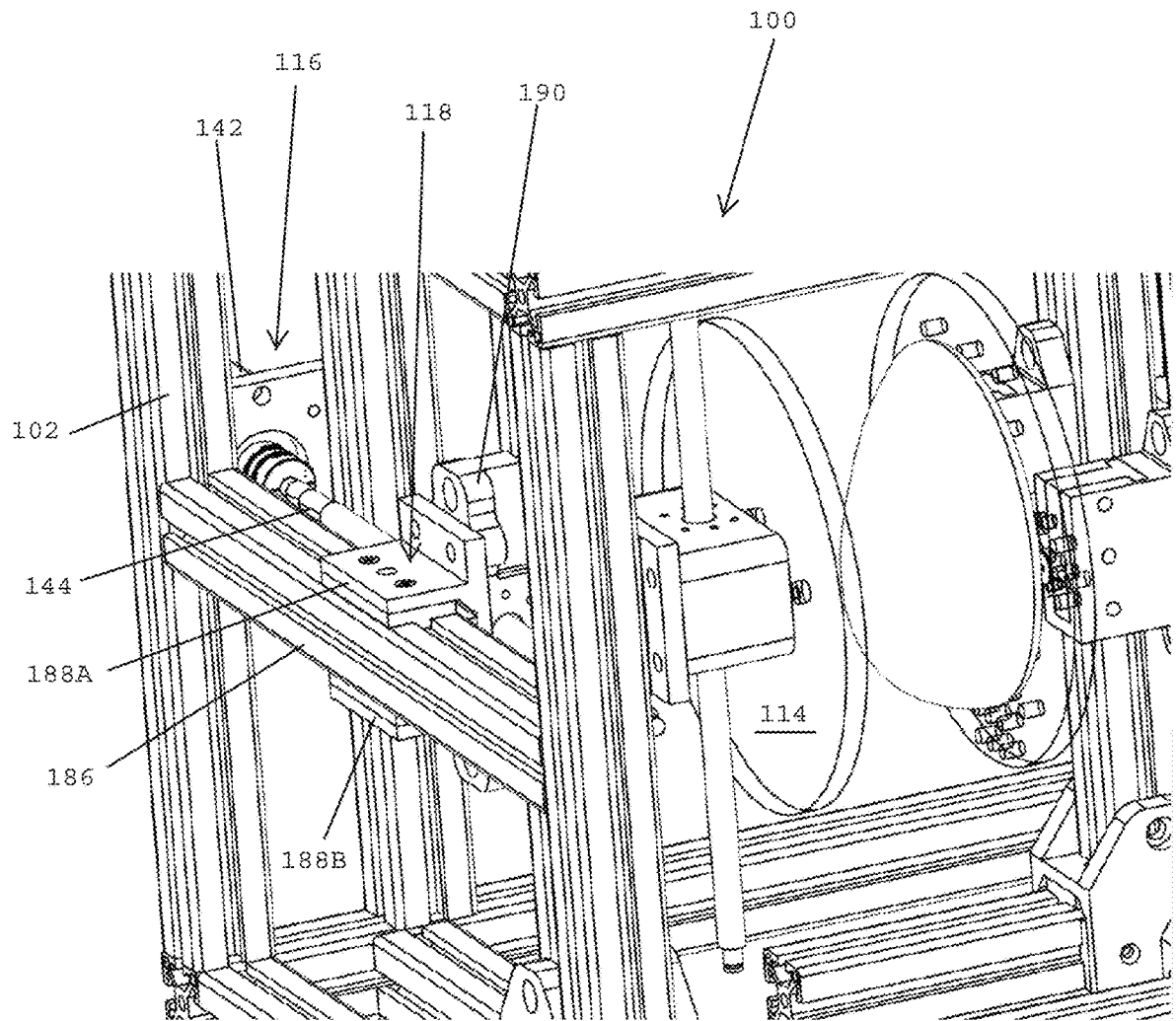
FIG. 11 is a perspective view of a second guide assembly and a compression plate of a test fixture, in accordance with one embodiment of the present patent application.
Figure 12:
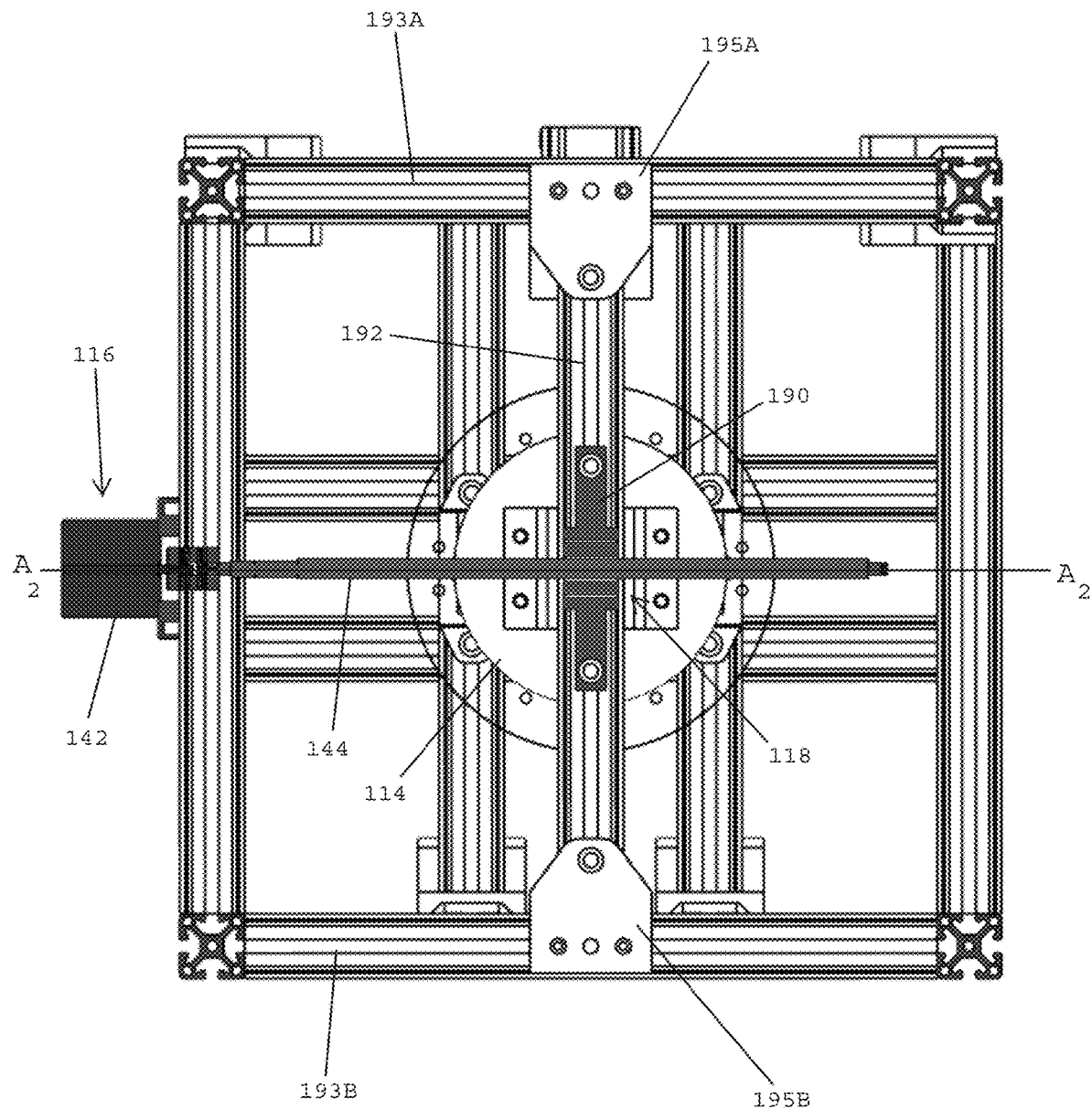
FIG. 12 is a cross-sectional view of a second actuator and a second guide assembly of a test fixture, in accordance with one embodiment of the present patent application.

Referring to FIGS. 11 and 12, in one embodiment, the test fixture 100 preferably includes the second actuator 116 that is configured to provide reciprocating motion to the compression plate 114 along the second axis $A_2$ (FIG. 1C), which may also be referred to as the X direction. In one embodiment, the second actuator 116 preferably includes the second stepper motor 142 that is coupled with the second externally threaded rod 144. In one embodiment, the second stepper motor 142 may be activated for rotating the second externally threaded rod 144 about its longitudinal axis. In one embodiment, the test fixture preferably includes the second guide assembly 118 that is preferably adapted to guide the reciprocating motion of the compression plate 114 along the second axis $A_2$. The second guide assembly 118 preferably includes a horizontally extending guide rail 186 that is mounted to the frame 102 of the test fixture 100. The second guide assembly 118 includes guide rail brackets 188A, 188B that are adapted to slide along the length of the horizontally extending guide rail 186 for guiding the reciprocating motion of the compression plate 114 along the second axis $A_2$ (FIGS. 1C and 12).

In one embodiment, the second externally threaded rod 144 is preferably adapted to mesh with internal threads of the compression plate mounting bracket 190. Referring to FIG. 12, in one embodiment, upper and lower ends of the vertical member 192 are coupled to the respective upper and lower guide rails 193A, 193B by respective upper and lower guide rail brackets 195A, 195B. As the second stepper motor 142 rotates the second externally threaded rod 144 about its longitudinal axis, the external threads of the second externally threaded rod 144 desirably mesh with the internal threads of the bracket 190 for moving the vertical member 192 along the second axis $A_2$, whereupon the upper slide rail bracket 195A preferably slides along the length of the upper guide rail 193A and the lower slide rail bracket 195B preferably slides along the length of the lower guide rail 193B of the second guide assembly 118.

Figure 13:
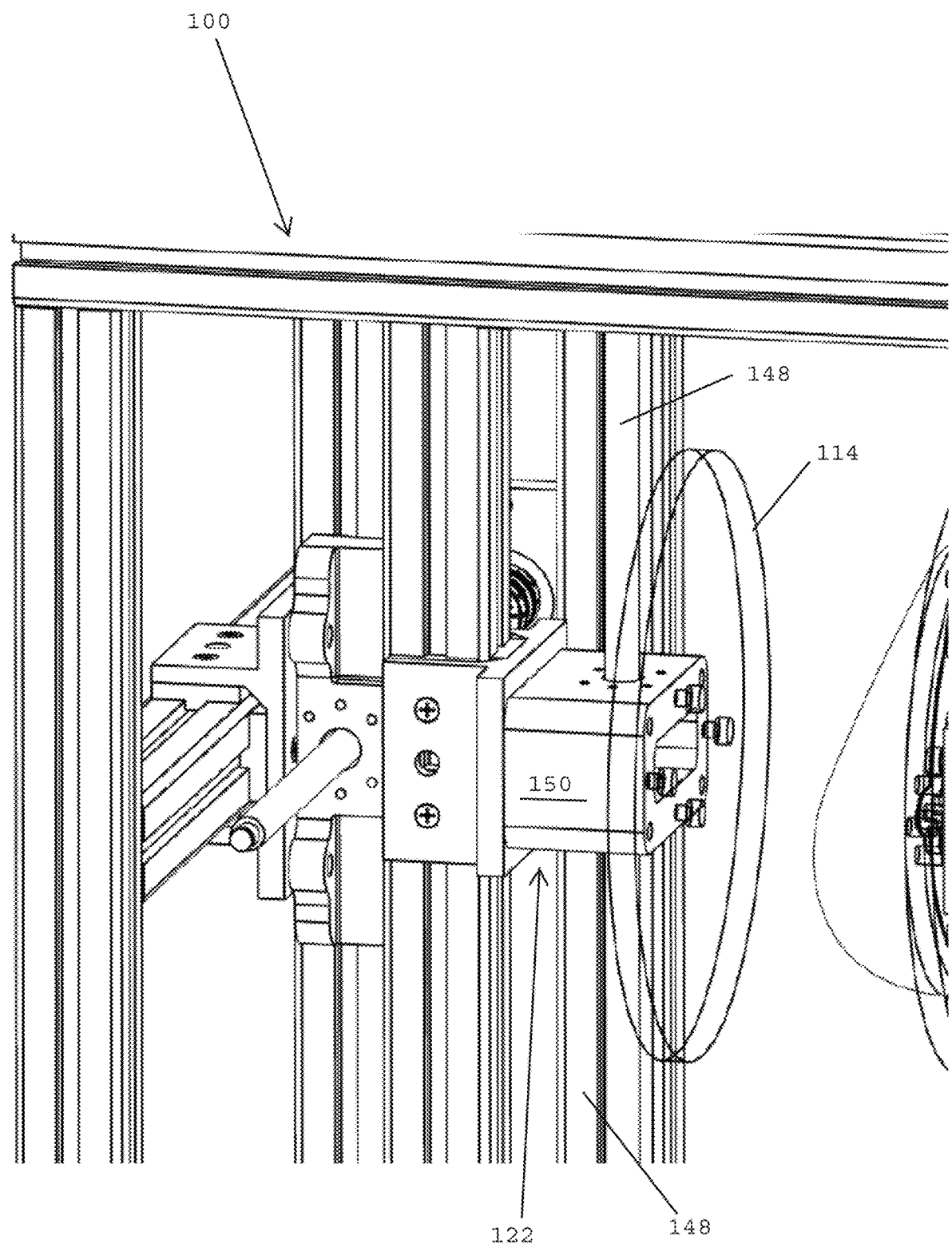
FIG. 13 is a perspective view of a third guide assembly and a compression plate of a test fixture, in accordance with one embodiment of the present patent application.
Figure 14:
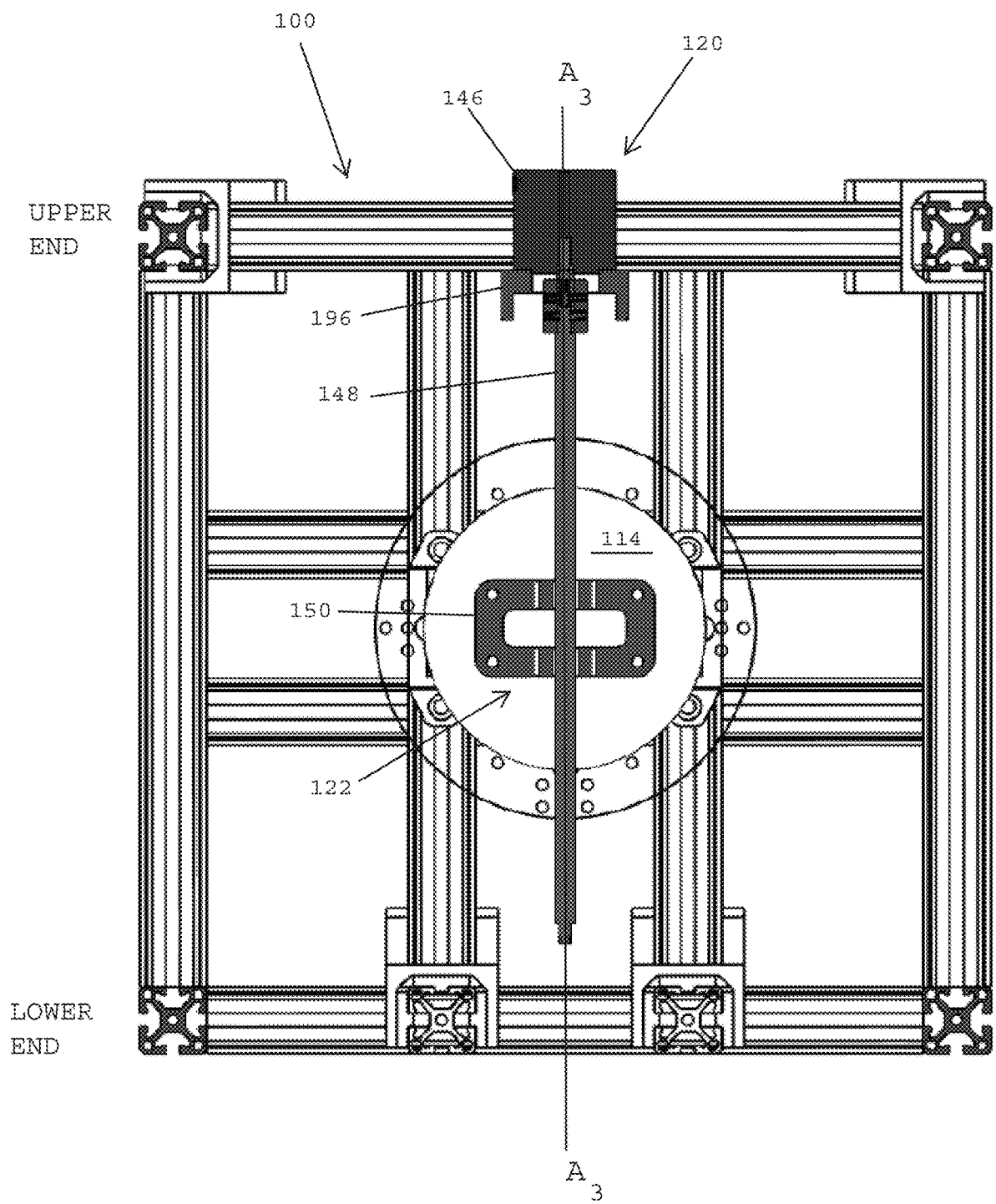
FIG. 14 is a cross-sectional view of a third actuator and a third guide assembly of a test fixture, in accordance with one embodiment of the present patent application.

Referring to FIGS. 13 and 14, in one embodiment, the test fixture 100 preferably includes a third actuator 120 (FIG. 1A) that is adapted to provide reciprocal motion to the compression plate 114 along the third axis $A_3$ (FIG. 1B), which may also be referred to as the Y direction. In one embodiment, the third actuator 120 preferably includes the third stepper motor 146 that is mounted to the frame 102 utilizing a third stepper motor mounting bracket 196. In one embodiment, the third actuator 120 preferably includes a third externally threaded rod 148. In one embodiment, activation of the third stepper motor 146 rotates the third externally threaded rod 148 about its longitudinal axis. In one embodiment, the breast implant test fixture 100 preferably includes a compression plate support bracket 150 that is utilized to secure the compression plate 114 to the third guide assembly 122, which guides reciprocal motion of the compression plate 114 along the third axis $A_3$ (FIG. 1B). In one embodiment, as the third externally threaded rod 148 rotate about its longitudinal axis, the external threads of the third externally threaded rod 148 mesh with internal threads of the mounting bracket 150 for moving the mounting bracket 150 up and down along the third axis $A_3$ (FIG. 1B).

Referring to FIG. 14, in one embodiment, the third stepper motor 146 is activated to rotate the third externally threaded rod 148 in a first direction about its longitudinal axis to move the compression plate 114 toward the upper end of the test fixture 100. In one embodiment, the third stepper motor 146 is activated to rotate the third externally threaded rod 148 in a second direction about its longitudinal axis (i.e., opposite the first direction of rotation) to move the compression plate 114 toward the lower end of the test fixture 100.

Figure 15:
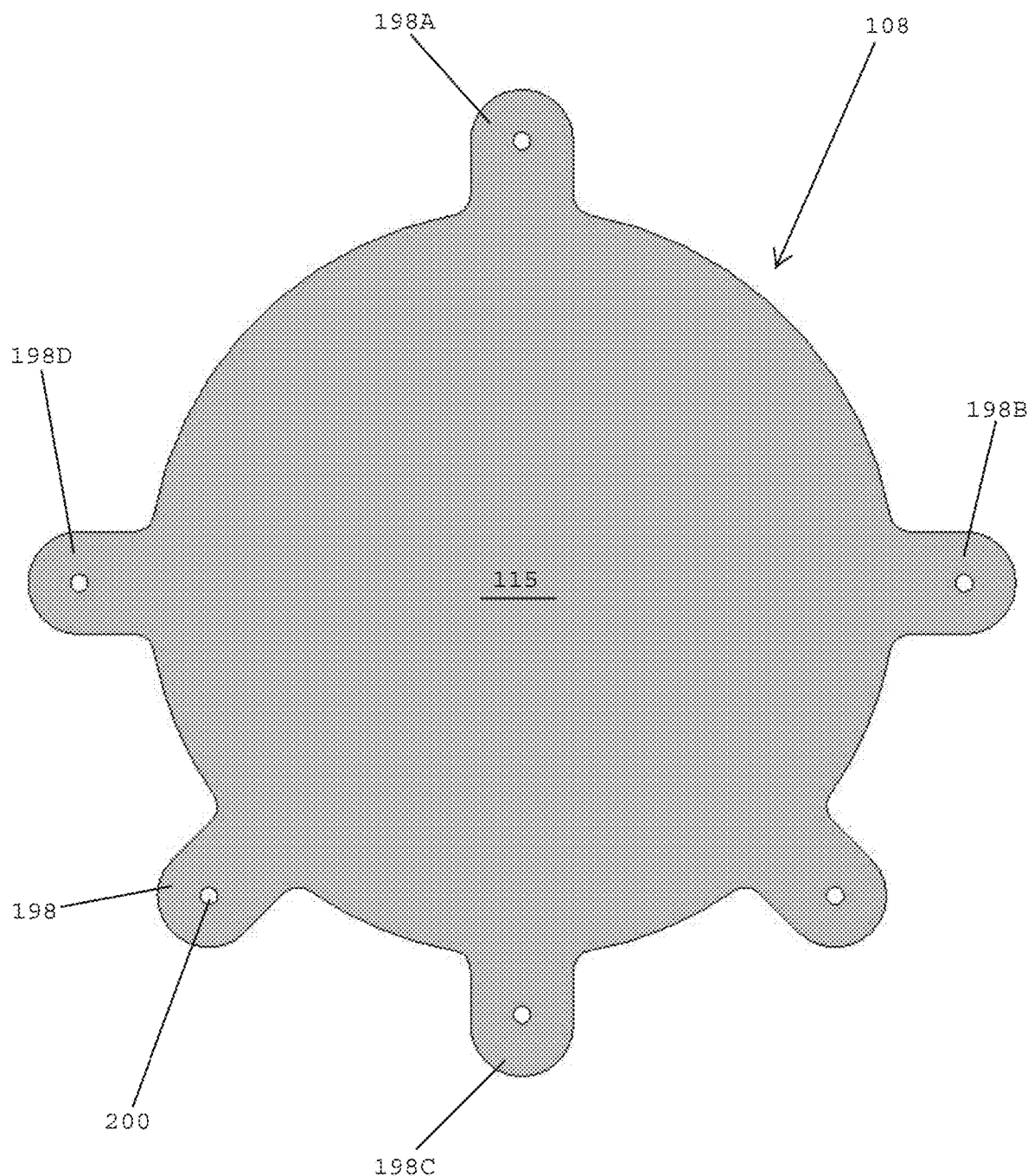
FIG. 15 is a top view of a breast implant having suture tabs, in accordance with one embodiment of the present patent application.

Referring to FIG. 15, in one embodiment, in order to mechanically assess an implant 108 (e.g., a breast tissue expander), the implant is preferably first secured to the base plate 106 of the test fixture 100 (FIG. 1A).

In one embodiment, the implant 108 preferably has a plurality of suture tabs 198, each tab having a suture tab hole 200. The implant 108 may be secured to the base plate 106 (FIG. 1A) by tying one or more suture knots through one or more of the suture tabs 198 and the implant mounting openings 174 (FIG. 8) that extend through the base plate 106. The suture knots may be tied using suture thread, such as size 0 suture sold under the trademark VICRYL®.

In one embodiment, suture tabs within four regions of the implant 108 (e.g., the 12, 3, 6, and 9 o'clock suture tabs) are preferably secured by sutures to the base plate 106 (FIG. 1A) in order to properly stress the implant during operation of the test fixture. In one embodiment, the four suture tabs that are secured by sutures to the base plate may include a first suture tab 198A located at the 12 o'clock position, a second suture tab 198B located at the 3 o'clock position, a third suture tab 198C located at the 6 o'clock position, and a fourth suture tab 198D located at the 9 o'clock position.

In one embodiment, prior to securing the implant 108 to the base plate, the implant may be removed from its packaging and at least slightly deflated so that only a small volume of air or fluid remains inside the shell 115 of the implant 108, which facilitates fixation of the implant to the base plate 106 (FIG. 1A).

In one embodiment, a total of three suture knots may be used for securing each suture tab 198A-198D to the base plate 106 (FIG. 1A), which ensures a strong fixation of the implant 108 to the base plate. One preferred method of forming the suture knots is shown below in FIGS. 16-21.

Referring to FIGS. 16 and 17, in one embodiment, a first suture knot may be formed by passing a first suture loop that through the suture tab hole 200 of the suture tab 198 and a first implant mounting opening 174A (e.g., the closest implant mounting opening), and then through a second implant mounting opening 174B that is adjacent the free end 202 of the suture tab 198.

Figure 19:
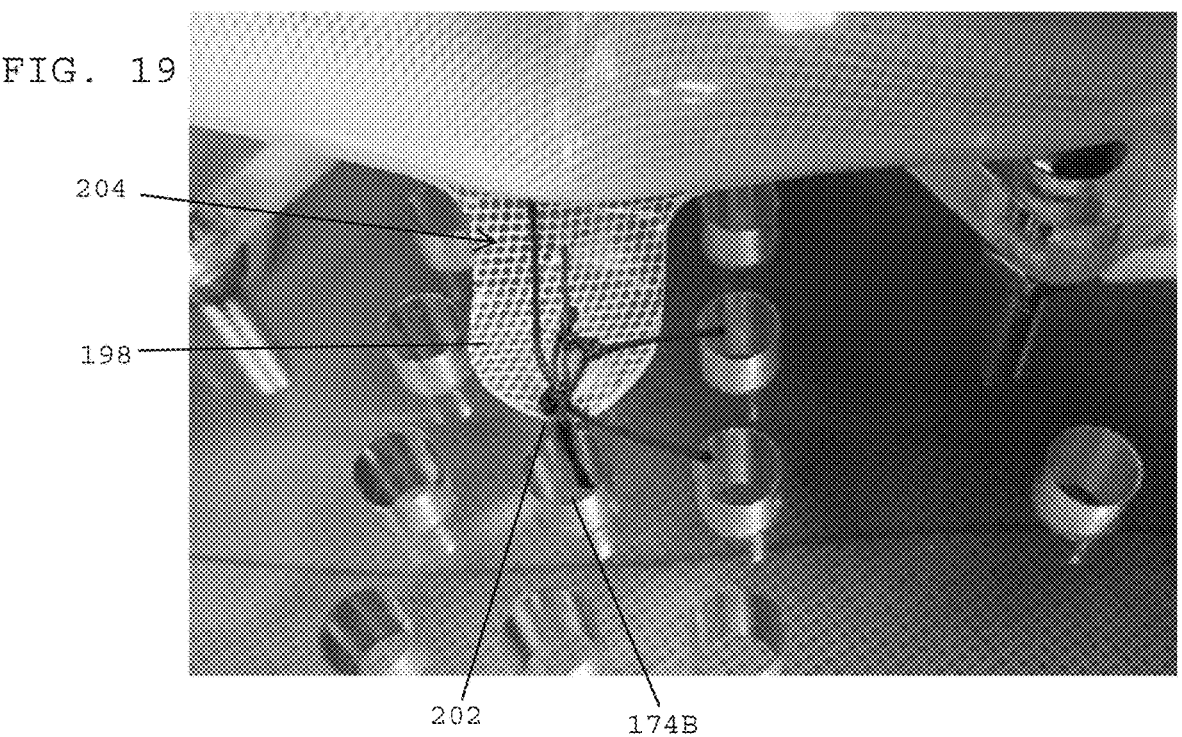
FIG. 19 shows the suture tab of FIG. 18 after the second stage of the method illustrated in FIG. 18 has been completed.

Referring to FIGS. 18 and 19, a second suture loop is passed through a proximal portion 204 of the suture tab 198 and a third implant mounting opening 174C, and is then passed through the second implant mounting opening 174B (FIG. 16) that is adjacent the free end 202 of the suture tab 198.

Figure 20:
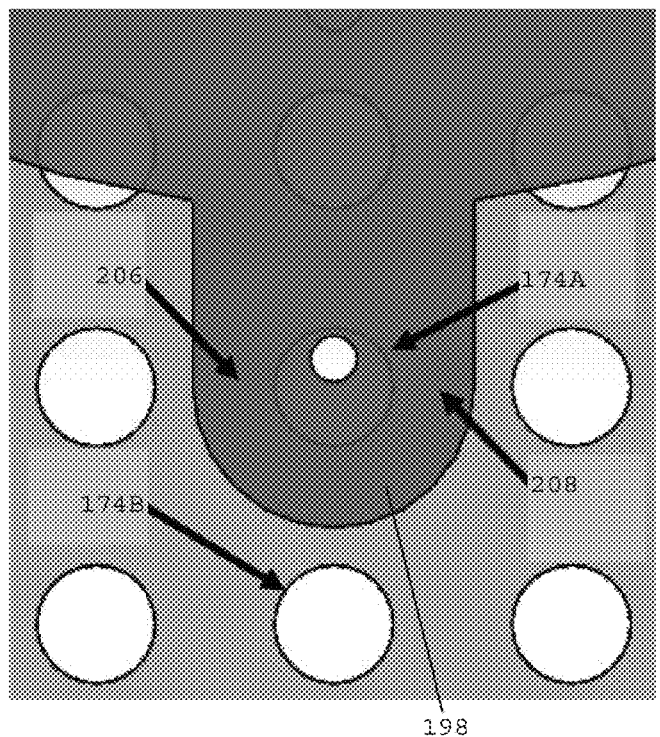
FIG. 20 is a schematic view of a third stage of a method of securing a suture tab of a breast implant to a base plate of a test fixture, in accordance with one embodiment of the present patent application.
Figure 21:
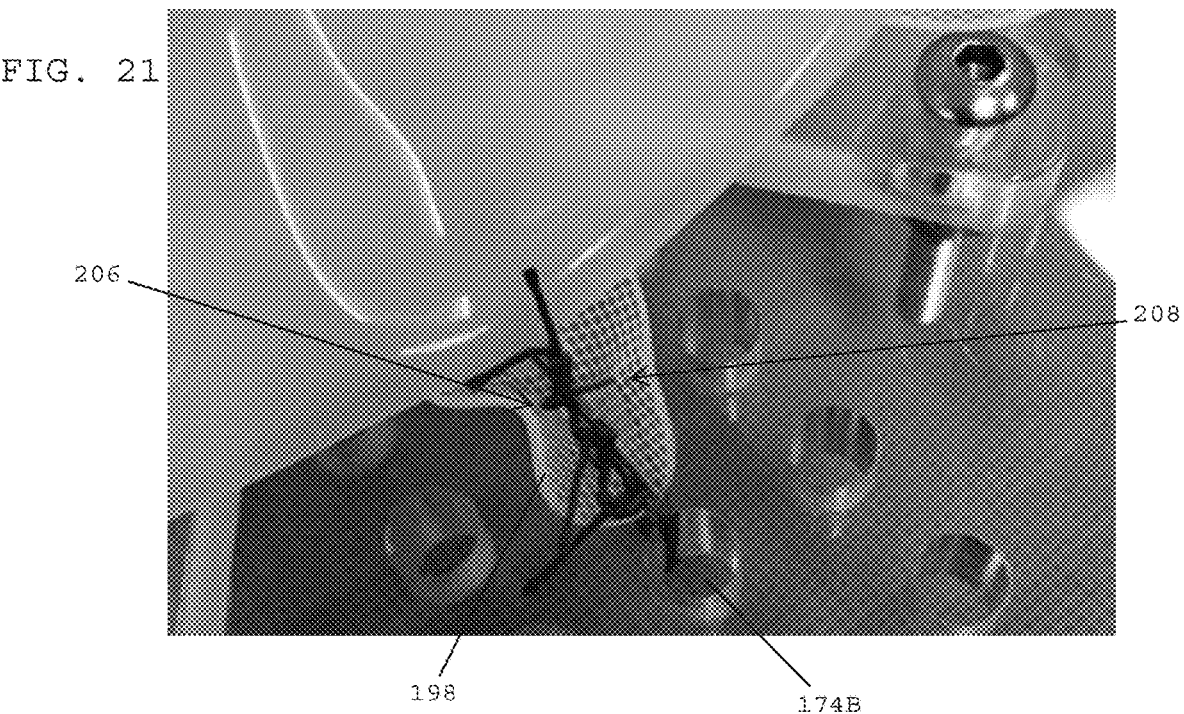
FIG. 21 shows the suture tab of FIG. 20 after the third stage of the method illustrated in FIG. 20 has been completed.

Referring to FIGS. 20 and 21, a third suture loop, which extends perpendicular to the longitudinal axis of the suture tab 198, may be formed. The third suture loop preferably passes through the left side 206 of the suture tab 198, through the first implant mounting opening 174A, out through the second implant mounting opening 174B, finally through the right side 208 of the suture tab 198.

The same suture knot as shown and described above in FIGS. 16-21 is preferably formed for each of the four suture tabs 198A-198D that are located at the 12, 3, 6, and 9 o'clock positions of the implant 108 (FIG. 15).

In one embodiment, prior to securing the implant to the base plate, the implant may be filled with a fluid (e.g., room temperature water) to a volume prescribed for the implant (e.g., plus or minus 3 cc).

Figure 22:
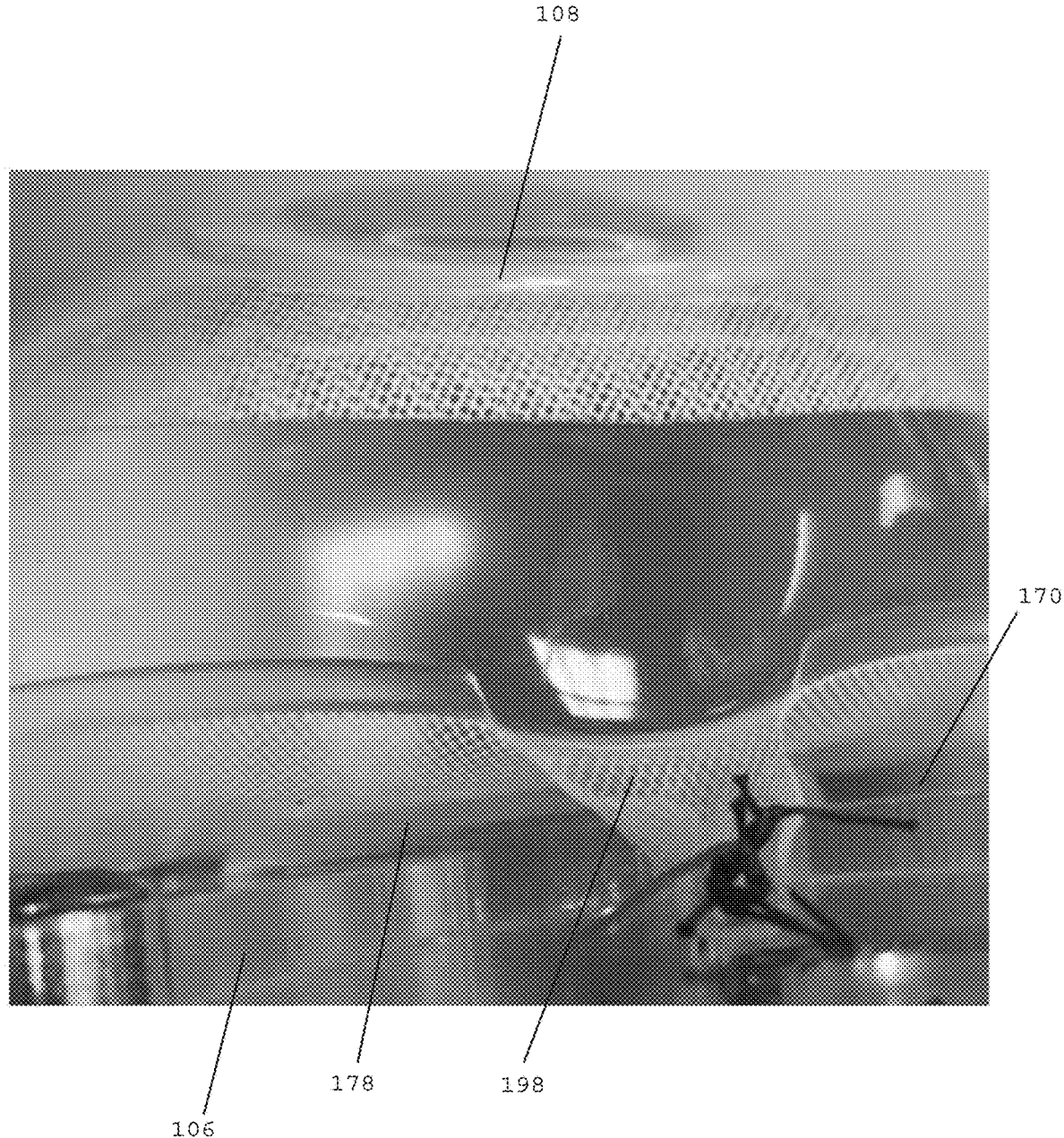
FIG. 22 shows a side view of the suture tab of FIG. 20 after the second stage of the method illustrated in FIG. 18 has been completed.

Referring to FIG. 22, in one embodiment, sutures are used for securing one or more suture tabs 198 of the implant 108 to the base plate 106. A chest wall plate 178 (FIGS. 10A and 10B) is preferably secured over the first major surface 170 of the base plate 106. The chest wall plate 178 is preferably positioned between the first major surface 170 of the base plate 106 and a posterior wall of the implant 108 for mimicking the anatomy of a patient and forming extra tension on the suture tabs 198 and the sutures utilized to secure the suture tabs of the implant 108 to the base plate 106.

Figure 23:
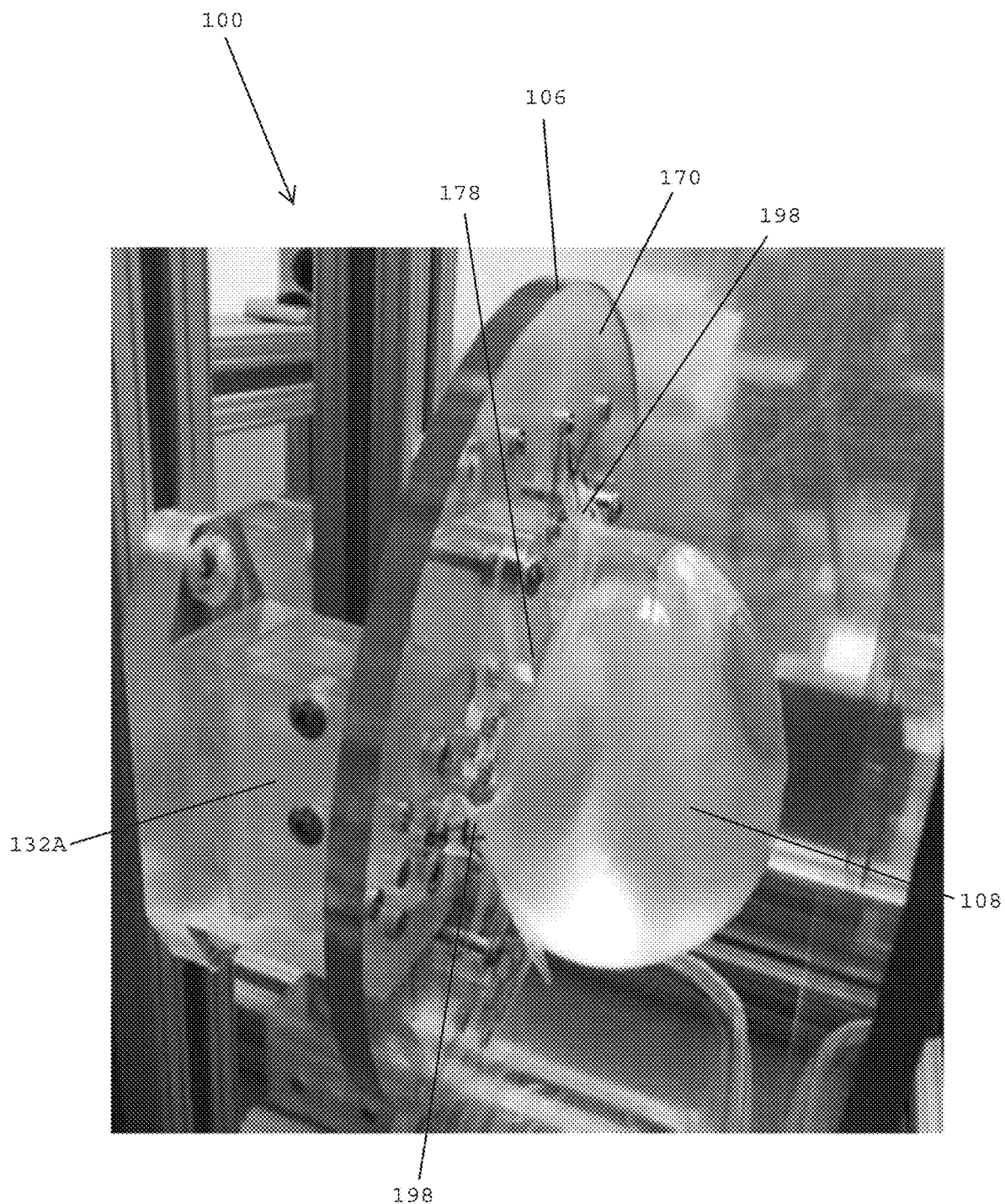
FIG. 23 is a perspective view of a base plate having a breast implant secured thereto and a chest wall plate secured between a first major face of the base plate and the breast implant for providing tension upon the suture tabs and the sutures utilized to secure the breast implant to the base plate, in accordance with one embodiment of the present patent application.

Referring to FIG. 23, in one embodiment, after the implant 108 has been secured over the first major surface 170 of the base plate 106, the base plate 106 may be loaded into the test fixture 100 by securing the base plate 106 to the base plate mounting brackets 132A, 132B (FIG. 1C) of the first guide assembly.

Figure 24:
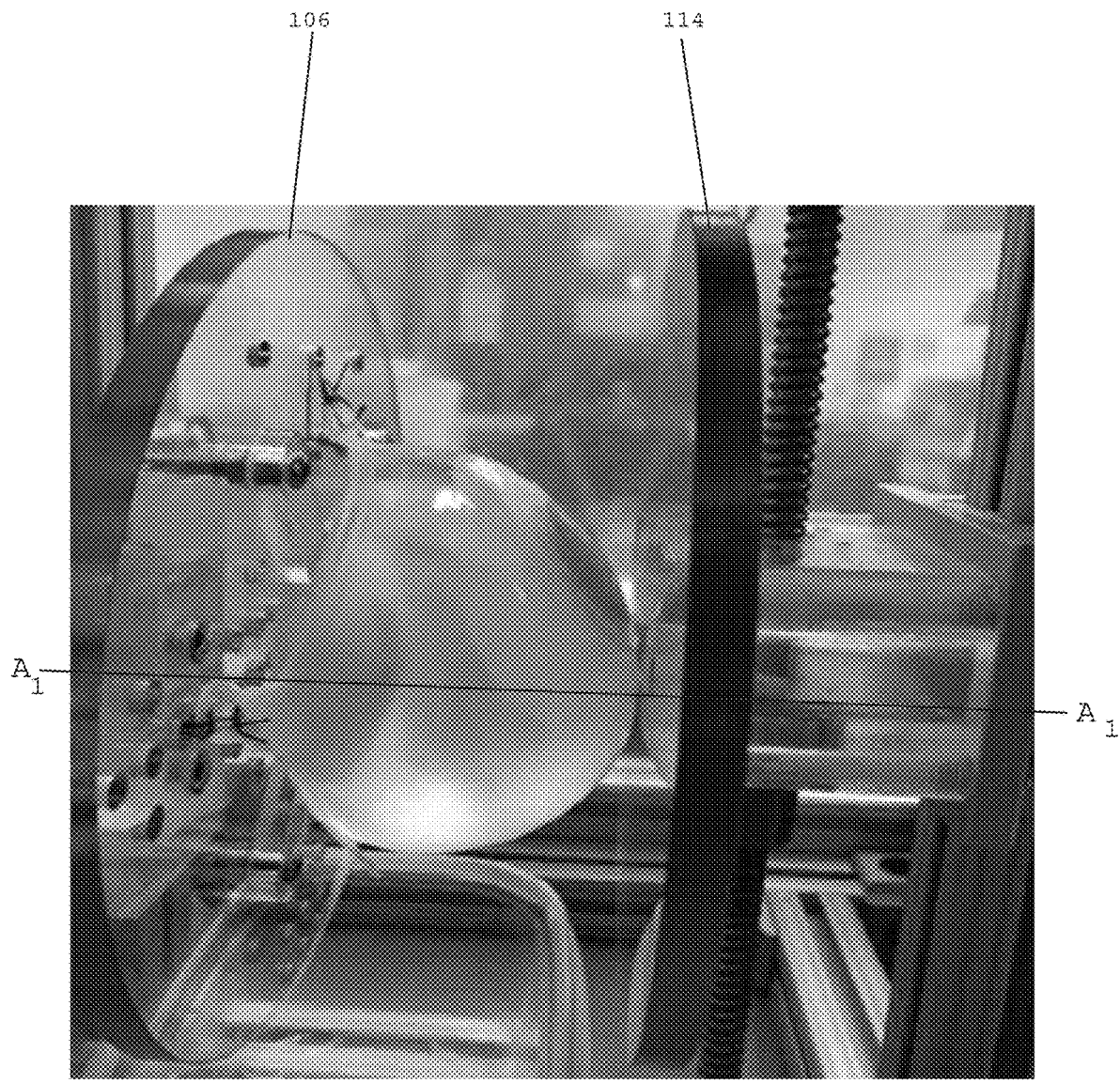
FIG. 24 shows a first stage of a method of mechanically evaluating a breast implant, in accordance with one embodiment of the present patent application.

Referring to FIG. 24, in one embodiment, the position of the base plate 106 along the first axis $A_1$ (FIG. 1C), also referred to herein as the Z-position, may be adjusted until the distal surface (e.g., the apex of the shell) of the implant 108 makes light contact with the opposing compression plate 114, which preferably constitutes the starting Z-position for testing the implant 108.

Figure 25:
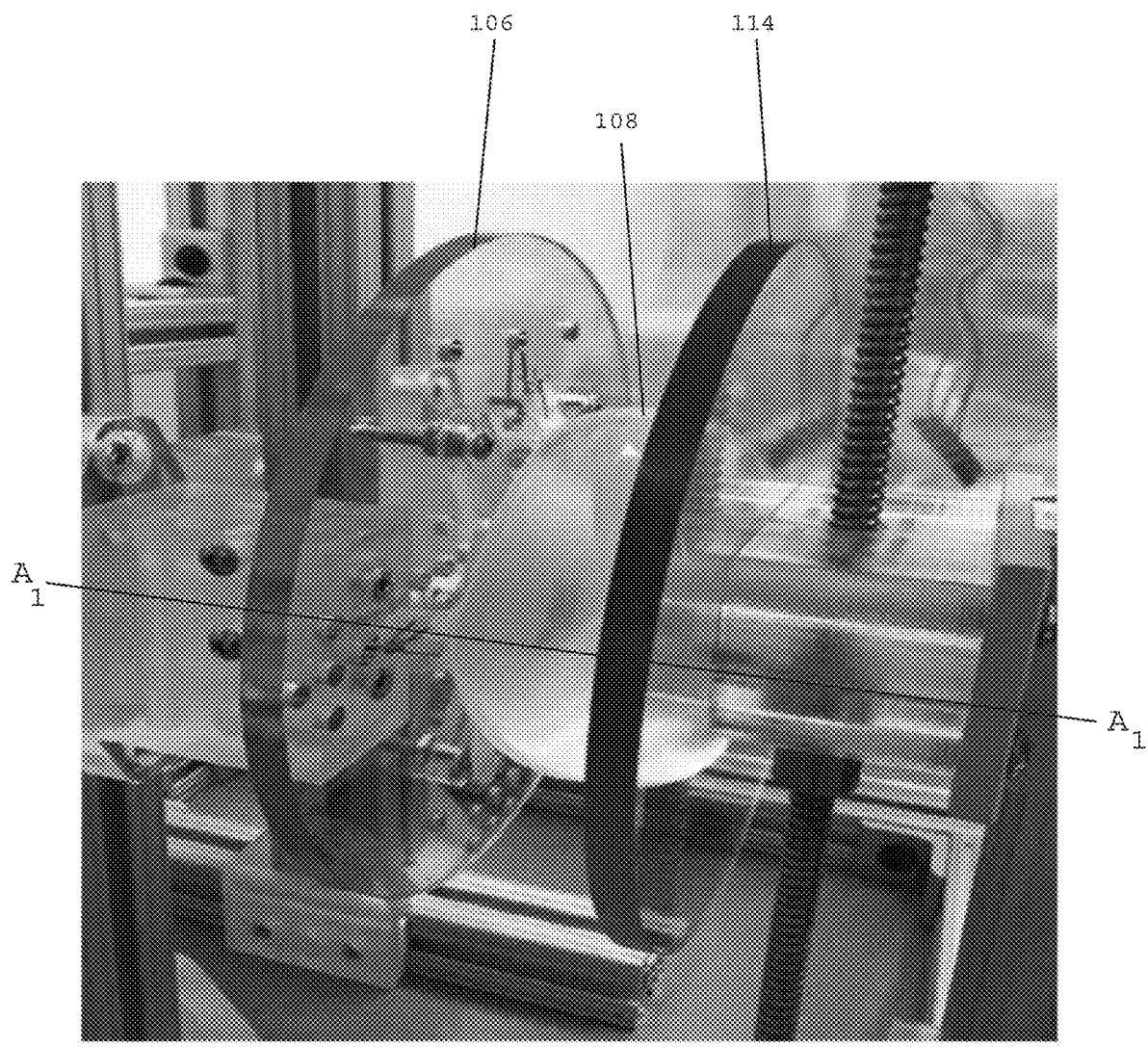
FIG. 25 shows a second stage of a method of mechanically evaluating a breast implant, in accordance with one embodiment of the present patent application.

Referring to FIG. 25, in one embodiment, the distance $D_1$ (FIG. 1B) between the base plate 106 and the opposing compression plate 114 may be reduced for compressing the implant 108 by a predetermined amount (e.g., 10-20 mm). FIG. 25 shows the implant 208 being compressed by 20 mm, whereupon the mechanical testing of the implant may commence.

Figure 26:
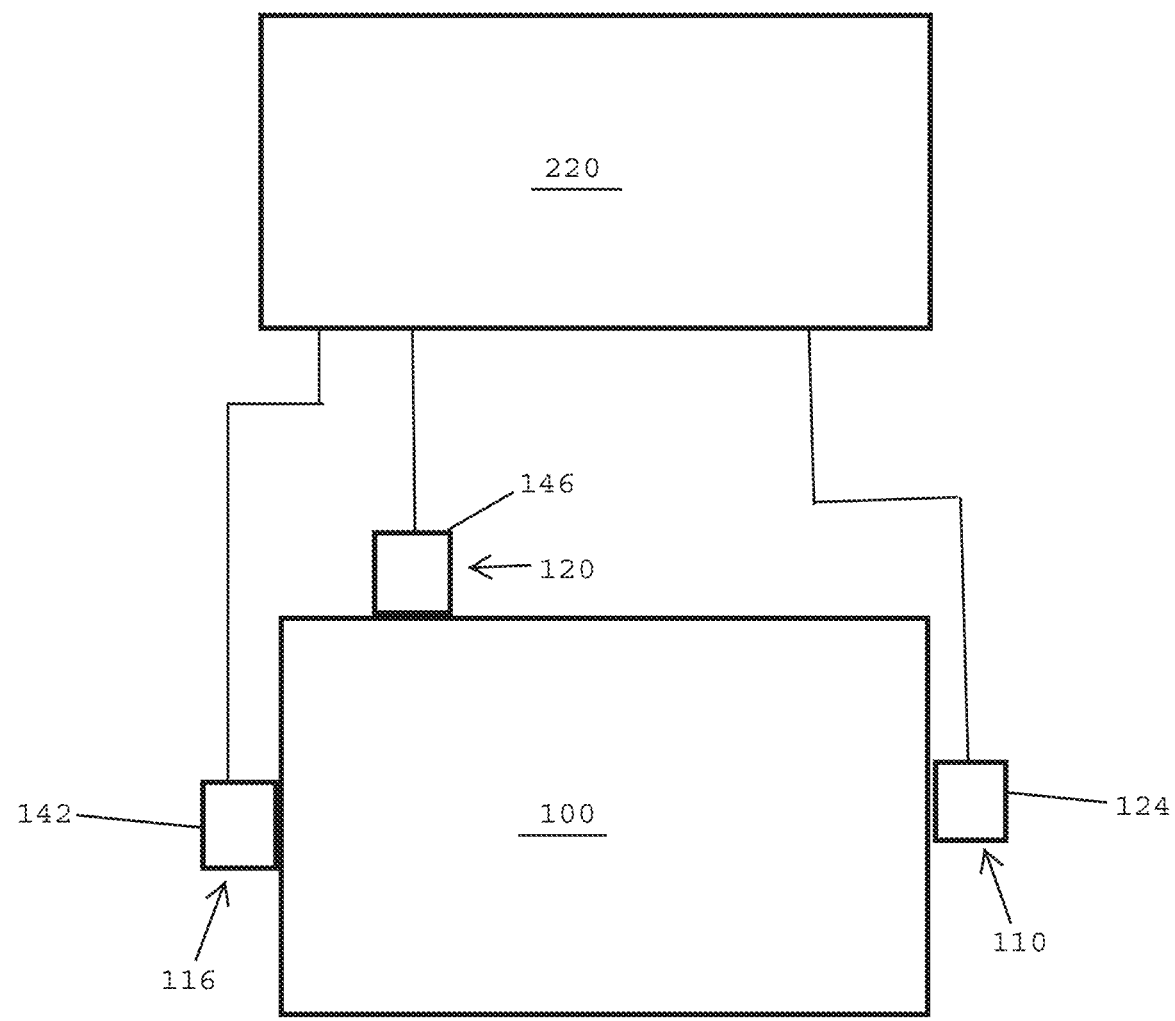
FIG. 26 is a schematic view of a system for mechanically evaluating a breast implant including a test fixture for the breast implant and a system controller, in accordance with one embodiment of the present patent application.

Referring to FIG. 26, in one embodiment, the test fixture 100 preferably includes a system controller 220 that controls the operation of the test fixture including the movement of the base plate along the first axis $A_1$ (FIG. 1B), and the movement of the compression plate along both the second axis $A_2$ (FIG. 1C) and the third axis $A_3$ (FIG. 1B). The system controller 220 may include one or more central processing units, one or more memory devices, and one or more software programs for controlling the operation of the test fixture. The test fixture may also include GPS technology for determining and/or controlling the exact location and movement of the base plate and the compression plate. In one embodiment, the system controller 220 is preferably in communication with the first actuator 110 (FIG. 1B), the second actuator 116 (FIG. 1C), and the third actuator 120 (FIG. 1C) of the test fixture 100 (FIG. 1A).

In one embodiment, the one or more software programs utilized to operate the test fixture may include a customized program known as the LabVIEW program. In one embodiment, the LabVIEW program is preferably in communication with Automation Direct STP-DRV 4850 stepper drivers, which, in turn communicate directly with the three stepper motors 124 (FIG. 1C), 142 (FIG. 1E), and 146 (FIG. 1F) of the test fixture. In one embodiment, the stepper motors may be NEMA 23 stepper motors. In one embodiment, the stepper drivers and the stepper motors may be powered by an Automation Direct STPPWR-4810 power supply.

In one embodiment, the LabVIEW program is designed for moving the compression plate 114 (FIG. 1C) in XY cycles. In one embodiment, the compression plate completes the number of inputted Y cycles and then the number of inputted X cycles, which constitutes one (1) XY cycle. The test fixture preferably runs the program until a selected number of XY cycles are completed.

For example, in one embodiment, if an operator selects 10 Y cycles, 10 X cycles, and 50 XY cycles, the test fixture will move as follows: 1) complete 10 Y cycles; 2) complete 10 X cycles; and 3) repeat this pattern 50 times (50 XY cycles). Thus, a full cycle consists of one (1) X cycle and one (1) Y cycle together. In one embodiment, one (1) XY cycle represents 10 cycles including 10 X and Y cycles completed.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A test fixture for mechanically testing breast implants comprising:
    a frame;
    a base plate coupled with said frame, said base plate having a first major surface;
    a first actuator coupled with said base plate for providing reciprocating motion to said base plate along a first axis;
    a compression plate coupled with said frame and opposing said base plate;
    a second actuator coupled with said compression plate for providing reciprocating motion to said compression plate along a second axis that intersects the first axis;
    a third actuator coupled with said compression plate for providing reciprocating motion to said compression plate along a third axis that intersects both the first axis and the second axis;
    a control system in communication with said first, second, and third actuators for controlling the movement of said base plate along the first axis and the movement of said compression plate along the second and third axes;
    wherein said base plate has two or more fixation points accessible at said first major surface of said base plate that are configured for securing a breast implant over said first major surface of said base plate.

2. The test fixture as claimed in claim 1, wherein said first actuator is configured for changing a distance between said base plate and said compression plate as said base plate moves along the first axis.

3. The test fixture as claimed in claim 2, wherein said first actuator comprises:
    a first stepper motor that is in communication with said control system;
    a first externally threaded rod extending along the first axis and being coupled with said first stepper motor and said base plate for guiding the reciprocating motion of said base plate along the first axis.

4. The test fixture as claimed in claim 3, wherein said second actuator comprises:

a second stepper motor that is in communication with said control system;
a second externally threaded rod being coupled with said second stepper motor and said compression plate for guiding reciprocating motion of said compression plate along the second axis.

5. The test fixture as claimed in claim 4, wherein said third actuator comprises:
a third stepper motor that is in communication with said control system;
a third externally threaded rod extending being coupled with said third stepper motor and said compression plate for guiding reciprocating motion of said compression plate along the third axis.

6. The test fixture as claimed in claim 1, wherein said compression plate has a major surface that directly opposes said first major surface of said base plate.

7. The test fixture as claimed in claim 6, wherein said first major surface of said base plate lies in a first plane and said major surface of said compression plate lies in a second plane that is parallel with the first plane.

8. The test fixture as claimed in claim 1, wherein said two or more fixation points are selected from the group consisting of two of more openings formed in said base plate and two or more protrusions projecting from said first major surface of said base plate.

9. The test fixture as claimed in claim 1, wherein said control system comprises a program for dynamically varying a distance between said base plate and said compression plate.

10. The test fixture as claimed in claim 1, wherein said control system comprises a program for dynamically varying the relative horizontal and vertical positions of said compression plate relative to said base plate.

11. The test fixture as claimed in claim 1, further comprising:
a breast implant secured over said first major surface of said base plate;
a chest wall plate disposed between the first major surface of said base plate and a posterior surface of said breast implant and projecting toward said compression plate that opposes said base plate.

12. The test fixture as claimed in claim 1, wherein said base plate has a central axis, and wherein said control system is configured for rotating said base plate around the central axis thereof.

13. The test fixture as claimed in claim 1, wherein said compression plate has a central axis, and wherein said control system is configured for rotating said compression plate around the central axis thereof.

14. The test fixture as claimed in claim 1, wherein the first axis defines the Z-axis coordinate of a Cartesian coordinate system for a three-dimensional space, the second axis defines the X-axis coordinate of the Cartesian coordinate system for the three-dimensional space, and the third axis defines the Y-axis coordinate of the Cartesian coordinate system for the three-dimensional space.

15. A test fixture for mechanically testing breast implants comprising:
a frame;
a base plate coupled with said frame, said base plate having a first major surface;
a compression plate coupled with said frame and opposing said base plate;
a control system in communication with said base plate and said compression plate, wherein said control system is configured for providing reciprocating motion to said base plate along a first axis, reciprocating motion to said compression plate along a second axis that intersects the first axis, and reciprocating motion to said compression plate along a third axis that intersects both the first axis and the second axis;
a breast implant secured over said first major surface of said base plate;
a chest wall plate disposed between the first major surface of said base plate and a posterior surface of said breast implant and projecting toward said compression plate that opposes said base plate.

16. The test fixture as claimed in claim 15, wherein said control system comprises:
a first actuator in communication with said control system, said first actuator being coupled with said base plate for providing the reciprocating motion to said base plate along the first axis;
a second actuator in communication with said control system, said second actuator being coupled with said compression plate for providing the reciprocating motion to said compression plate along the second axis that intersects the first axis; and
a third actuator in communication with said control system, said third actuator being coupled with said compression plate for providing reciprocating motion to said compression plate along a third axis that intersects both the first axis and the second axis.

17. The test fixture as claimed in claim 16, wherein said control system comprises a program that is in communication with said first actuator for dynamically varying the distance between said base plate and said compression plate along the first axis.

18. The test fixture as claimed in claim 15, wherein the first axis defines the Z-axis coordinate of a Cartesian coordinate system for a three-dimensional space, the second axis defines the X-axis coordinate of the Cartesian coordinate system for the three-dimensional space, and the third axis defines the Y-axis coordinate of the Cartesian coordinate system for the three-dimensional space.

19. A test fixture for mechanically testing breast implants comprising:
a frame;
a base plate coupled with said frame, said base plate having a first major surface;
a first actuator coupled with said base plate for providing reciprocating motion to said base plate along a first axis;
a compression plate coupled with said frame and opposing said base plate;
a second actuator coupled with said compression plate for providing reciprocating motion to said compression plate along a second axis that intersects the first axis;
a third actuator coupled with said compression plate for providing reciprocating motion to said compression plate along a third axis that intersects both the first axis and the second axis;
a control system in communication with said first, second, and third actuators for controlling the movement of said base plate along the first axis and the movement of said compression plate along the second and third axes;
a breast implant secured over said first major surface of said base plate;
a chest wall plate disposed between the first major surface of said base plate and a posterior surface of said breast implant and projecting toward said compression plate that opposes said base plate.

\* \* \* \* \*